United States Patent
Halpern et al.

(10) Patent No.: US 6,365,151 B1
(45) Date of Patent: Apr. 2, 2002

(54) CELLULAR IMMUNOGENS COMPRISING COGNATE PROTO-OXOGENES

(75) Inventors: Michael S Halpern, West Newton, MA (US); James M England, Media, PA (US)

(73) Assignee: Philadelphia Health and Educational Corporation, Philadelphia, PA (US)

( * ) Notice: Subject to any disclaimer, the term of this patent is extended or adjusted under 35 U.S.C. 154(b) by 0 days.

(21) Appl. No.: 09/167,322

(22) Filed: Oct. 7, 1998

Related U.S. Application Data

(63) Continuation-in-part of application No. 09/101,226, filed on Jul. 2, 1998, now abandoned, which is a continuation-in-part of application No. PCT/US97/00582, filed on Jan. 13, 1997.
(60) Provisional application No. 60/010,262, filed on Jan. 19, 1996.

(51) Int. Cl.$^7$ .................. A61K 35/00; A61K 48/00; C12N 15/85; C12N 15/63

(52) U.S. Cl. .................. 424/93.21; 424/93.2; 435/325; 435/320.1; 514/44

(58) Field of Search .................. 435/325, 320.1; 424/93.2, 93.21; 514/44

(56) References Cited

U.S. PATENT DOCUMENTS

| | | | |
|---|---|---|---|
| 5,593,972 A | | 1/1997 | Weiner et al. ................. 514/44 |
| 5,693,522 A | * | 12/1997 | Chada et al. ................ 435/325 |

FOREIGN PATENT DOCUMENTS

| | | |
|---|---|---|
| EP | 0 119 702 | 9/1984 |
| WO | WO 92/14756 | 9/1992 |

OTHER PUBLICATIONS

Gelman et al. (1993) Oncogene, vol. 8 (11), 2995–3004, 1993.*
Gilbert et al. (1994) J. Exp. Med., vol. 179, 249–258, Jan. 1994.*
Fuchs et al. (1992) Science, vol. 258, 1156–1159, 1992.*
Verma et al. (1997) Science, vol. 389, 239–242, Sep. 1997.*
Marshall et al. (1995) Science, vol. 269, 1050–1055, 1993.*
Orkin et al. (1995) "Report and Recommendations to the . . . ", Dec. 1995.*
Freidmann et al. (1997) Scien. Am., vol., 96–101, Jun. 1997.*
Restifo et al. (1993) J. Immunother., vol. 14, 182–190, 1993.*
Yasumotomi et al. (1995) J. Virol., vol. 69(4), 2279–2284, 1995.*
Felgner et al., "Lipofection: A highly efficient, lipid–mediated DNA–transfection procedure", Proc. Natl. Sci. USA, vol. 84, pp 7413–7417, Nov. 1987.

Kuzumaki et al., "Transplantation Resistance to a Rous Sarcoma Virus–Induced Tumor in Mice Immunized with v–src Protein", J. Natl. Cancer Inst., 1988, vol. 80, No. 12, pp 959–962.
Fendly et al., "The extracellular domain of HER2/neu is a potential immunogen for active specific immunotherapy of breat cancer", J. Biol. Response Mod., Oct. 1990, vol. 9, No. 5, pp 449–455.
Malone et al., "Cationic liposome–mediated RNA transfection,", Proc. Natl. Acad. Sci. USA, Aug. 1989, vol. 86, pp 6077–6081.
Temin, "Overview of biological effects of addition of DNA molecules to cells", J. Med. Virol., May 1990 , vol. 31, pp 13–17.
Wisner et al., Tumor Immunity Generated in the Course of Regression of v–src–Induced Sarcomas, J. of Virol., vol. 65, No. 12, Dec. 1991, pp 7020–7024.
Halpern et al., "Immune–Based Resistance to the Formation of v–src –Induced Distal Tumors", Virology 197, 1993, pp 480–484.
Disis et al., "In vitro Generation of Human Cytolytic T–Cells Specific for Peptides Derived From the HER–2/neu Protooncogene Protein", Cancer Research, 54, Feb. 15, 1994, pp 1071–1076.
Taylor et al., "Major Histocompatibility (B) complex control of the Formation of v–src–Induced Metastases", Virology, 205, 1994, pp 569–573.
Plachy et al. Src–specific immunity in inbred chickens bearing v–src DNA and RSV–induced tumors:, Immunogenetics, 40, 1994, pp 257–265.

(List continued on next page.)

Primary Examiner—Karen M. Hauda
Assistant Examiner—Anne-Marie S Beckerleg
(74) Attorney, Agent, or Firm—Drinker Biddle & Keath LLP

(57) ABSTRACT

A cellular immunogen is provided for immunizing a host against the effects of the product of a target proto-oncogene, where the overexpression of the target proto-oncogene is associated with a malignancy. The cellular immunogen comprises host cells which have been transfected with at least one transgene construct comprising a transgene cognate to the target proto-oncogene and a strong promoter to drive the expression of the transgene in the transfected cells. The transgene encodes a gene product which induces host immunoreactivity to host self-determinants of the product of the target proto-oncogene gene. The transgene may comprise, for example, wild-type or mutant retroviral oncogene DNA cognate to the target proto-oncogene; or wild-type or mutant proto-oncogene DNA of a species different from the host species. The cellular immunogen may be prepared from biopsied host cells, e.g. skin fibroblasts, which are stably or transiently transfected with the transgene construct containing the cognate transgene. The host cells transfected with the cognate transgene construct, are then returned to the body of the host to obtain expression of the cognate transgene in the host.

22 Claims, 4 Drawing Sheets

OTHER PUBLICATIONS

Peoples et al., "Breast and ovarian cancer–specific cytotoxic T lymphocytes recognize the same HER2/neu–derived peptide", *Proc. Natl. Acad. Sci., USA*, vol. 92, Jan. 1995, pp 432–436.

Conry, et al., "Characterization of a messenger RNA polynucleotide vaccine vector", *Cancer Res.*, vol. 55, Apr. 1, 1995, pp 1397–1400.

McCabe et al., "Minimal Determinant Expressed by a Recombinant Vaccinia Virus Elicts Therapeutic Antitumor Cytolytic T Lymphocyte Response", *Cancer Research*, 55, Apr. 15, 1995, pp 1741–1747.

Fenton et al. "Cytotoxic T–cell Response and In Vitro Protection Against Tumor Cells Harboring Activated ras Proto–oncogenes", *J. Natl. Cancer Inst.*, 85(16) 1993 pp 1294–1302.

Halpern et al. "Endogenous c–src as a determinant of the tumorigenicity of src oncogenes", *Proc. Natl. Acad. Sci., USA*, 93(2) Jan. 23, 1996 pp 824–827.

Disis et al., Existent T–Cell and Antibody Immunity to HER–2/neu Protein in Patients with Breast Cancer, *Cancer Research* 54, Jan. 1, 1994 pp 16–20.

\* cited by examiner

CELLULAR IMMUNOGENS COMPRISING COGNATE PROTO-OXOGENES

CROSS-REFERENCE TO RELATED APPLICATION

This is a continuation-in-part of our application Ser. No. 09/101,226, filed on Jul. 2, 1998, now ABN.; which is a CIP of PCT/US97/00582 filed Jan. 13, 1997; which claims benefit to Provisional application Ser. No. 60/010,262 filed Jan. 19, 1996.

FIELD OF THE INVENTION

The invention relates to the field of cancer vaccination and immunotherapy.

BACKGROUND OF THE INVENTION

A current goal of cancer research is the identification of host factors that either predispose to tumor formation or serve to enhance tumor growth.

Genes that confer the ability to convert cells to a tumorigenic state are known as oncogenes. The transforming ability of a number of retroviruses has been localized in individual viral oncogenes (generally v-onc). Cellular oncogenes (generally c-onc) present in many species are related to viral oncogenes. It is generally believed that retroviral oncogenes may represent escaped and/or partially metamorphosed cellular genes that are incorporated into the genomes of transmissible, infectious agents, the retroviruses.

Some c-onc genes intrinsically lack oncogenic properties, but may be converted by mutation into oncogenes whose transforming activity reflects the acquisition of new properties, or loss of old properties. Amino acid substitution can convert a cellular proto-oncogene into an oncogene. For example, each of the members of the c-ras proto-oncogene family (H-ras, N-ras and K-ras) can give rise to a transforming oncogene by a single base mutation.

Other c-onc genes may be functionally indistinguishable from the corresponding v-onc, but are oncogenic because they are expressed in much greater amounts or in inappropriate cell types. These oncogenes are activated by events that change their expression, but which leave their coding sequence unaltered. The best characterized example of this type of proto-oncogene is c-myc. Changes in MYC protein sequence do not appear to be essential for oncogenicity. Overexpression or altered regulation is responsible for the oncogenic phenotype. Activation of c-myc appears to stem from insertion of a retroviral genome within or near the c-myc gene, or translocation to a new environment. A common feature in the translocated loci is an increase in the level of c-myc expression.

Gene amplification provides another mechanism by which oncogene expression may be increased. Many tumor cell lines have visible regions of chromosomal amplification. For example, a 20-fold c-myc amplification has been observed in certain human leukemia and lung carcinoma lines. The related oncogene N-myc is five to one thousand fold amplified in human neuroblastoma and retinoblastoma. In human acute myeloid leukemia and colon carcinoma lines, the proto-oncogene c-myb is amplified five to ten fold. While established cell lines are prone to amplify genes, the presence of known oncogenes in the amplified regions, and the consistent amplification of particular oncogenes in many independent tumors of the same type, strengthens the correlation between increased expression and tumor growth.

Immunity has been successfully induced against tumor formation by inoculation with DNA constructs containing v-onc genes, or by inoculation with v-onc proteins or peptides. A series of reports describe a form of "homologous" challenge in which an animal test subject is inoculated with either v-src oncoprotein or DNA constructs containing the v-src gene. Protective immunity was induced against tumor formation by subsequent challenge with v-src DNA or v-src-induced tumor cells. See, Kuzumaki et al., *JNCI* (1988), 80:959–962; Wisner et al., *J. Virol.* (1991), 65:7020–7024; Halpern et al., *Virology* (1993), 197:480–484: Taylor et al., *Virology* (1994), 205:569–573; Plachy et al., *Immunogenetics* (1994), 40:257–265. A challenge is said to be "homologous" where reactivity to the product of a targeted gene is induced by immunization with the same gene, the corresponding gene product thereof, or fragment of the gene product. A challenge is "heterologous" where reactivity to the product of a targeted gene is induced by immunization with a different gene, gene product or fragment thereof.

WO 92/14756 (1992) describes synthetic peptides and oncoprotein fragments which are capable of eliciting T cellular immunity, for use in cancer vaccines. The peptides and fragments have a point mutation or translocation as compared to the corresponding fragment of the proto-oncogene. The aim is to induce immunoreactivity against the mutated proto-oncogene, not the wild-type proto-oncogene. WO 92/14756 thus relates to a form of homologous challenge.

EP 119,702 (1984) describes synthetic peptides having an amino acid sequence corresponding to a determinant of an oncoprotein encoded by an oncogenic virus, which determinant is vicinal to an active site of the oncoprotein. The active site is a region of the oncoprotein required for oncoprotein function, e.g., catalysis of phosphorylation. The peptides may be used to immunize hosts to elicit antibodies to the oncoprotein active site. EP 119,702 is thus directed to a form of homologous challenge.

The protein product encoded by a proto-oncogene constitutes a self antigen and, depending on the pattern of its endogenous expression, would be tolerogenic at the level of T cell recognition of the self peptides of this product. Thus, vaccination against cancers which derive from proto-oncogene overexpression is problematic.

Recent attempts have been made to induce immunity in vitro or in vivo to the product of the HER-2/neu proto-oncogene. The proto-oncogene encodes a 185-kDa transmembrane protein. The HER-2/neu proto-oncogene is over-expressed in certain cancers, most notably breast cancer. In each report discussed below, the immunogen selected to induce immunity comprised a purified peptide of the $p185^{HER-2/neu}$ protein, and not a cellular immunogen.

Disis et al., *Cancer Res.* (1994) 54:16–20 identified several breast cancer patients with antibody immunity and CD4+helper/inducer T-cell immunity responses to $p185^{HER-2/neu}$ protein. Antibodies to $p185^{HER-2/neu}$ were identified in eleven of twenty premenopausal breast cancer patients. It was assumed prior to this work that patients would be immununologically tolerant to HER-2/neu as a self-protein and that immunity would be difficult to generate.

Disis et al., *Cancer Res.* (1994) 54:1071–1076 constructed synthetic peptides identical to $p185^{HER-2/neu}$ protein segments with amino acid motifs similar to the published motif for HLA-A2.1-binding peptides. Out of four peptides synthesized, two were shown to elicit peptide-specific cytotoxic T-lymphocytes by primary in vitro immunization in a culture system using peripheral blood lymphocytes from a normal individual homozygous for HLA-A2. Thus, it was concluded that the p185$^{HER-2/neu}$ proto-oncogene protein contains immunogenic epitopes capable of generating human CD8+ cytotoxic T-lymphocytes.

The cytotoxic T cells elicited in the latter report were not, however, shown to recognize tumor cells, but only targets that bound the synthesized peptides. Other work (Dahl et al., *J. Immunol.* (1996), 157:239–246) has demonstrated that cytotoxic cells may recognize targets that bind peptide but fail to recognize targets that endogenously synthesize peptide. It is thus unclear whether the cytotoxic cells elicited by Disis et al. would be capable of recognizing tumor cells. In any event, no protection against tumor growth was demonstrated by Disis et al.

Peoples et al., *Proc. Natl. Acad. Sci. USA* (1995), 92:432–436, report the identification of antigenic peptides presented on the surface of ovarian and breast cancer cells by HLA class I molecules and recognized by tumor-specific cytotoxic T lymphocytes. Both HLA-A2-restricted breast and ovarian tumor-specific cytotoxic T lymphocytes recognized shared antigenic peptides. T cells sensitized against a nine-amino acid sequence of one of the peptides demonstrated significant recognition of HLA-A2 HER2/neu tumors.

It remains unclear whether Peoples et al. have successfully attacked proto-oncogene-encoded self, as the immunizing peptide which is expressed in the tumor cells contained an isoleucine at position 2, whereas the peptide expressed in normal tissue contains valine residue at this position. Moreover, although stimulation of T cells occurred in vitro, this stimulation does not represent a true primary immune response insofar as the starting T cell population represented tumor infiltrating lymphocytes.

The research accounts of Disis et al. and Peoples et al. required a form of in vitro stimulation, either priming as described by Disis et al., or restimulation as described by Peoples et al. The in vitro protocols of Disis et al. and Peoples et al. require a mutant cell line to aid in selection of the peptide which will serve to induce reactivity. Non-mutant, peptide antigen-presenting cells have their HLA class I molecules already loaded with endogenous peptides, a phenomenon which precludes exogenous loading from without. The value of the mutant lines is that they lack the TAP genes (encoding the transporters associated with antigen presentation). Class I binding of internally-derived peptides is significantly lowered, and "empty" class I molecules are present on the cell surface and available for binding of exogenously added peptides. This availability of peptide binding sites on membrane-bound class I allows examination of whether a given peptide will (i) even bind to class I, and (ii) function as a target in cytotoxic T cell assays. However, the need for a mutant cell line for deduction of candidate immunizing peptide sequences limits the usefulness of peptide-based immunization schemes.

Fendly et al., *J. Biol. Response Modifiers* (1990), 9:449–455 present an account of a polypeptide-based immunotherapy. Purified polypeptide corresponding to the extracellular domain of the p185$^{HER-2/neu}$ protein was obtained from a transfected cell line. The purified peptide was employed in the immunization of guinea pigs. The immunized animals developed a cellular immune response, as monitored by delayed-type hypersensitivity. Antisera derived from immunized animals specifically inhibited the in vitro growth of human breast tumor cells overexpressing p185$^{HER-2/neu}$. There is no indication by Fendly et al. of induction of self versus non-self reactivity. It is likely that the guinea pigs were chiefly responding to non-self determinants (as defined in terms of the guinea pig host) on the human polypeptide immunogen.

The use of peptides for immunization is of necessity limited to immunization with a single haplotype. There are approximately thirty HLA types in man. In each case of peptide immunization, one must be careful to select peptides which match the host HLA type. The selected peptide must be immunogenic in the host and be capable of presentation to host immune system cells.

What is needed is an immunization method for immunizing humans and animals against self-encoded proto-oncogenes which are associated with the development of cancer, which dispenses with the need for isolating immunogenic, HLA host-matched peptides for immunization.

SUMMARY OF THE INVENTION

It is an object of the invention to induce reactivity to self-determinants of the product of an overexpressed proto-oncogene.

It is an object of the invention to provide for a form of therapy or prophylaxis based upon the capacity to induce immune reactivity to proto-oncogene-encoded self as overexpressed in tumor cells.

It is an object of the invention to provide a cellular immunogen for use in immunization against self proto-oncogene determinants.

It is an object of the invention to provide for a method for vaccinating a host against disease associated with the overexpression of a proto-oncogene.

These and other objects will be apparent from the following disclosure.

A method of vaccinating a host against disease associated with the overexpression of a target proto-oncogene is provided. The method comprises:

(a) excising cells from the host;

(b) transfecting the excised cells with at least one transgene construct comprising at least one transgene cognate to the target proto-oncogene and a strong promoter to drive the expression of the transgene in the transfected cells, the transgene encoding a gene product which induces host immunoreactivity to host self-determinants of the product of the target proto-oncogene gene;

(c) returning the excised cells transfected with the transgene construct to the body of the host to obtain expression of the transgene in the host.

According to one principal embodiment of the invention, the transgene comprises wild-type or mutant retroviral oncogene DNA. According to another principal embodiment of the invention, the transgene comprises wild-type or mutant proto-oncogene DNA of a species different from the host species. Where the transgene comprises mutant retroviral oncogene DNA or mutant proto-oncogene DNA, the mutant DNA is preferably nontransforming. The mutant DNA preferably comprises a deletion mutation in a region of the DNA which is essential for transformation. Preferably, the host cells are transfected with a plurality, most preferably at least five, different transgene constructs, each construct encoding a different deletion mutation.

In one preferred embodiment of the invention, the mutant DNA has at least about 75% homology, more preferably at least about 80% homology, most preferably at least about 90% homology, with the corresponding wild-type oncogene or proto-oncogene DNA.

The invention is further directed to a cellular immunogen for immunizing a host against the effects of the product of a target proto-oncogene, the overexpression of which is associated with a cancer. The cellular immunogen comprises the host cells which have been transfected with at least one transgene construct, as described above.

The invention is also directed to a method of preparing the cellular immunogen, by (a) excising cells from the host, and (b) transfecting the excised cells with at least one transgene construct, as described above.

The cells transfected with the transgene are preferably rendered non-dividing prior to return to the body of the host.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

The term "cognate" as used herein refers to a gene sequence that is evolutionarily and functionally related between species. For example but not limitation, in the human genome. the human c-myc gene is the cognate gene to the mouse c-myc gene, since the sequences and structures of these two genes indicate that they are highly homologous and both genes encode proteins which are functionally equivalent.

By "homology" is meant the degree of sequence similarity between two different amino acid sequences, as that degree of sequence similarity is derived by the FASTA program of Pearson and Lipman, *Proc. Natl. Acad. Sci. USA* (1988), 85:2444–2448, the entire disclosure of which is incorporated herein by reference.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

The word "transfection" is meant to have its ordinary meaning, that is, the introduction of foreign DNA into eukaryotic cells.

By "transgene" is meant a foreign gene that is introduced into one or more host cells.

By "transgene construct" is meant DNA containing a transgene and additional regulatory DNA, such as promoter elements, necessary for the expression of the transgene in the host cells.

DETAILED DESCRIPTION OF THE INVENTION

Figure 1A:
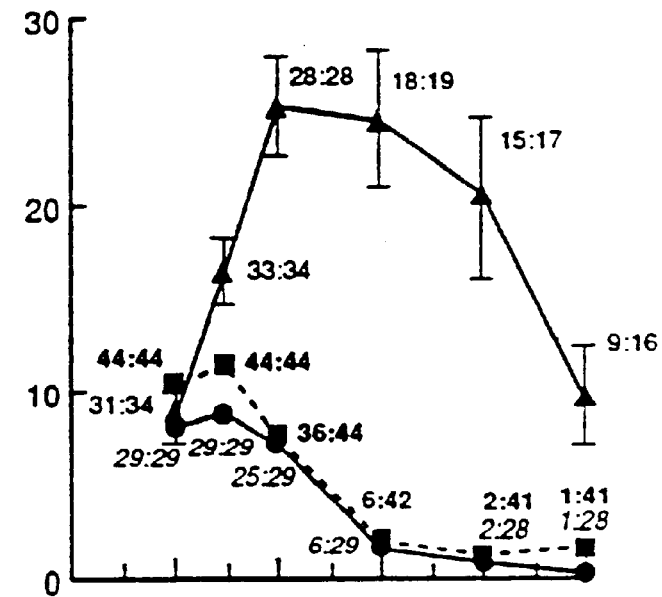
FIGS. 1A and 1B are plots of the mean tumor diameter over time following subcutaneous wing web inoculation of 1-day-old line TK (FIG. 1A) and line SC (FIG. 1B) chickens with 100 μg of tumorigenic plasmids pcsrc527 (—▲—), pVSRC-C1 (—●—) or pMvsrc (—■—). The mean tumor diameter (mm) at a particular time point and for any one group of TK or SC line chickens inoculated was computed as the sum of the diameters of the primary tumors divided by the number of chickens surviving to that point. The ratios at each time point show, for a particular group, the number of chickens bearing palpable tumors to the total number of survivors to that point (standard typeface for pcsrc527, italics for pVSRC-C1, bold typeface for pMVsrc). Error bars (unless obscured by the symbol) indicate standard error.

A vaccination strategy is provided to prevent development of cancers. The vaccination method may be carried out on a subject at risk for a particular cancer, but before the development of the cancer. The practice of the invention may serve for the immnunoprevention of prevalent human cancers, such as colon carcinoma, breast carcinoma, and various lymphomas whose progress is accompanied by the overexpression of a cellular proto-oncogene.

The vaccination strategy of the present invention relies on the induction of an immune response that targets tumor cells by virtue of the recognition of the proto-oncogene-specific antigenicity. The aim of the vaccine protocol is to induce reactivity to self-determinants of an overexpressed proto-oncogene product. The strategy exploits the structural relatedness between the product of the cellular proto-oncogene and that of the product of genes cognate to the target proto-oncogene. The cognate gene may comprise a wild-type or mutant cognate retroviral oncogene or a wild-type or mutant proto-oncogene of a species different from the host species. The starting point of the vaccine strategy is the high degree of primary sequence homology that exists between the protein product of a targeted proto-oncogene and that of its cognate retroviral oncogene, or between the proto-oncogene product and the product of a cognate proto-oncogene from a different species. However, in contrast to other proposed vaccine strategies, the present invention is not based on the immune recognition of a determinant defined by a cancer specific mutation.

For those tumors showing proto-oncogene overexpression, this sequence homology permits application of the following strategy, which can be employed either prophylactically or therapeutically under conditions of cell-surface expression, or other forms of adjuvanicity, as chosen to enhance immunogenicity: (a) immunization of host biopsied cells with a DNA construct comprising a transgene cognate to the target proto-oncogene, which transgene encodes a gene product which induces host immunoreactivity to host self-determinants of the product of the target proto-oncogene; (b) return of the transfected cells to the body of the host to obtain expression of the transgene in the host, and thus immunity against the proto-oncogene product. The invention relies on the targeting of a self-determinant found on an overexpressed or overabundant proto-oncogene-encoded product. The foreign peptide elements of the immunizing oncogene product will trigger peripheral lymphocytes exhibiting a weak cross reactivity for the self peptides of the targeted proto-oncogene product. Although such self peptides would be present in normal cells expressing the proto-oncogene, targeting of the tumor cells is favored in view of their overexpression of the proto-oncogene.

The immune strategy exploits the antigenicity of two alternative types of determinants: (1) tumor-associated antigenic determinant(s) induced as a consequence of the activity of the oncogene product, e.g., an enzymatic modification of a cellular protein effected by the oncogene product, or (2) tumor associated antigenic determinant(s) intrinsic to the oncogene-encoded product itself. The difficulty in exploiting the first alternative by traditional means, i.e., antigen purification, is that at present little or no systematic information exists bearing on the properties of an antigen that, though oncogene-induced, is not oncogene-encoded. This situation makes purification of any such antigen problematic. However, this problem is obviated from the outset by the present invention which utilizes biopsied cells which, as transfected in culture by the cognate retroviral oncogene, would express the relevant antigenicity.

In terms of exploiting the second alternative, that of an antigenicity intrinsic to the proto-oncogene product, a relevant consideration is that the protocol of immunization according to the present invention primes the host to determinants of the oncogene product itself. A consequence of this immunization is induction of T-cell reactivity to the divergent, i.e foreign, peptide determinants of the retroviral oncogene product, i.e., those peptide determinants that show sequence differences with the positionally homologous determinants of the cellular proto-oncogene product. The induction of this reactivity does not in itself have vaccine potential, since the foreign determinants specific to the retroviral oncogene product are normally absent from the cellular proto-oncogene product. Nevertheless, the foreign peptide elements, notably those that differ by only a single amino acid from the positionally homologous self peptides, trigger peripheral T-lymphocytes exhibiting a weak cross-reactivity for the self peptides. Although such self peptides are present in normal cells expressing the proto-oncogene, targeting of the tumor cells is favored in view of their overexpression of the proto-oncogene.

It is possible that many tumor-associated and overexpressed proto-oncogenes might possess mutations. In some cases, overexpression may very well arise as a direct consequence of one or more of the mutations. However, the present vaccination method does not have as its object the deliberate targeting of non-self determinants generated by proto-oncogene mutations. Unlike prior vaccination methods designed to target such mutation-driven non-self determinants, it is the aim of the present invention to induce reactivity for self-determinants in the overexpressed product of tumor associated and overexpressed proto-oncogenes.

Prior efforts attempting to elicit reactivity to proto-oncogene self determinants have relied on in vitro protocols utilizing mutant cell lines to identify individual self peptide immunogens (Disis et al., *Cancer Res.* (1994) 54:1071–1076; Peoples et al., *Proc. Natl. Acad. Sci USA* (1995), 92:432–436). According to the present invention, the host immune system is presented with the full array of naturally-derived class I binding peptides. The vaccine strategy of the present invention obviates the need for any a priori assessment of the immunogenicity of individual peptides.

While the cellular immunogens of the invention display self peptides, non-self peptides would also be presented which may serve as more effective tolerance breakers. The value of a non-self, but closely related to self, peptide is that it may more readily activate those T cells that have both a weak cross reactivity for the cognate self peptide and an activation threshold (determined by the tightness of binding to the T cell receptor) too high to be triggered by the self peptide. Moreover, cognate non-self is inductive of a good immune response, simply because it does in fact constitute nonself. The non-self immune response is expected to predispose the induction of the inevitably weaker response to the self determinants on the same protein product, since the resultant cytokine release provides local help to initiate the weaker anti-self response.

As hereinafter exemplified in a model of src-oncogene-based tumor formation, immunization with cells transfected with a transgene construct expressing the v-src oncogene product induces reactivity to the product of the c-src proto-oncogene, thereby conferring protection against the growth of tumors displaying overexpression of the c-src proto-oncogene. As also illustrated, immunization with cells transfected with a transgene construct expressing the human mdm-2 proto-oncogene product induces reactivity to the product of the murine mdm-2 proto-oncogene, thereby conferring protection against the growth of murine tumors displaying overexpression of the murine mdm-2 proto-oncogene.

Target Proto-Oncogenes

According to the present invention, patients with a family history of a cancer characterized by the overexpression of a particular proto-oncogene are selected for immunization. Alternatively, patients whose tumors can be shown to overexpress the proto-oncogene are selected. Overexpression of a proto-oncogene may derive from an increase over a basal level of transcription. Overexpression may also derive from gene amplification, that is, an increase in gene copy number, coupled with a basal or elevated level of transcription. Proto-oncogene overexpression may be assayed by conventional probing techniques, such as described in *Molecular Cloning: A Laboratory Manual* J. Sambrook et al., eds., Cold Spring Harbor Laboratory Press, 2nd ed. 1989. The level of target proto-oncogene expression may be determined by probing total cellular RNA from patient cells with a complementary probe for the relevant mRNA. Total RNA from the patient cells is fractionated in a glyoxal/agarose gel, transferred to nylon and hybridized to an appropriately labelled nucleic acid probe for the target mRNA. The number of relevant mRNA transcripts found in the patient cells is compared to that found in cells taken from the same tissue of a normal control subject.

As an alternative to measuring MRNA transcripts, the expression level of a target proto-oncogene may be assessed by assaying the amount of encoded protein which is formed. Western blotting is a standard protocol in routine use for the determination of protein levels. See *Molecular Cloning*, supra, Chapter 18, incorporated herein by reference. Accordingly, a cell lysate or other cell fraction containing protein is electrophoresed on a polyacrylamide gel, followed by protein transfer to nitrocellulose, and probing of the gel with an antibody specific for the protein in question. The probe step permits resolution of the desired protein from all other proteins in the starting mixture. The bound antibody may be prelabeled, e.g., by a radioisotope such as $^{125}$I, so as to permit its detection on the gel. Alternatively, a secondary reagent (usually an anti-immunoglobin or protein A) may be radiolabeled or covalently coupled to an enzyme such as horseradish peroxidase or alkaline phosphatase. The strength of the signal is proportional to the amount of the target protein. The strength of the signal is compared with the signal from a sample analyzed in the same manner, but taken from normal as opposed to tumor tissue.

A description of the methodology and use of Western blotting to determine the levels of the c-src-encoded protein pp60$^{c-src}$ in adenomatous polyps (colonic epithelia) is provided by Cartwright et al., *Proc. Natl. Acad. Sci. USA* (1990), 87:558–562, the entire disclosure of which is incorporated herein by reference.

An at least about eight-fold increase in that gene's expression in the patient cells compared to expression in normal control cells from the same tissue would indicate candidacy for vaccination.

Table 1 includes a partial list of representative proto-oncogenes, the overexpression of which has been associated with one or more malignancies. Each listed proto-oncogene is a target proto-oncogene according to the present invention. The corresponding oncogene, of which the target proto-oncogene is the normal cellular homolog, is also identified. This list of target proto-oncogenes is intended to be representative, and not a complete list.

TABLE 1

Representative List of Target Proto-Oncogenes

| Proto Oncogene | Tumor | Comments/References |
|---|---|---|
| AKT-2 | ovarian | v-Akt is the oncogene of the AKT8 virus, which induces lymphomas in mice. 1. Bellacosa et al., (1995) Int. J. Cancer 64(4):280–5: Southern-blot analysis has shown AKT-2 amplification in 12.1% of ovarian carcinomas, while Northern bot analysis has revealed overexpression of AKT-2 in 3 of 25 fresh ovarian carcinomas which were negative for AKT-2 amplification. 2. Cheng et al., (1996) Proc. Natl. Acad. Sci. USA 89(19):9267–71): Amplification of AKT-2 has been detected in 10% of pancreatic carcinomas. |
| AKT-2 | pancreatic | Cheng et al., (1996) Proc. Natl. Acad. Sci. USA 93(8):3636–41: Amplification of AKT-2 has been detected in 10% of pancreatic carcinomas. |
| c-erbB-2 | bladder | c-ErbB-2 is also known as HER2/neu. V-erbB is the oncogene of the avian erythroblastosis virus. 1. Underwood et al., (1995) Cancer Res. 55(11):2422–30: Protein overexpression was observed in 45% of patients with non-recurrent disease and 50% of patients with recurrent disease; 9% of bladder tumors analyzed showed gene amplification. 2. Coombs et al., (1993) Pathology 169(1):35–42: c-ErbB-2 gene amplification was observed in 14% of bladder tumors analyzed. 3. Gardiner et al., (1992) Urolog. Res. 20(2):17–20: Nineteen percent of primary transitional cell bladder carcinomas showed c-erbB-2 gene amplification. |
| c-erbB-2 | breast | 1. Molina et al., (1966) Anticancer Research 16(4B):2295–300: Abnormal c-erbB-2 levels were found in 9.2% of patients with locoregional breast carcinoma, and in 45.4% of patients with advanced disease. 2. DePotter et al., (1995) Virchows Arch. 426(2):107–15: Overexpression of the oncoprotein is observed in about 20% of invasive duct cell carcinomas of the breast. 3. Bandyopadhyay et al., (1994) Acta Oncol. 33(5):493–8: 35.4% of breast tumors showed c-erbB-2 overexpression: 17.4% showed gene amplification. 4. Fontana et al., (1994) Anticancer Res. 14(5B):2099–104: 26% of samples showed c-erbB-2 amplification. 5. Press et al., (1993) Cancer Research 53(20):4960–70: Amplified overexpression was identified in 38% of primary breast cancers. 6. Berns et al., (1992) Cancer Res. 52(5):1107–13: 23% of primary breast cancer tissues exhibited amplification. 7. Delvenne et al., (1992) Eur. J. of Cancer 28(2-3):700–5: c-erbB-2 mRNA was overexpressed in 34% of breast tumor samples. 8. Inglehart, (1990) Cancer Res. 50(20):6701–7: Two to thirty-two-fold gene amplification was found in multiple stages of tumor progression. 9. Slamon et al., (1989) Science 244:707–12: A 28% incidence of amplification of c-erbB-2 was found in 189 primary breast cancers. 10. Kraus et al., (1987) EMBO J. 6(3):605–1O: Eight cell lines demonstrated c-erbB-2 mRNA levels ranging from 4 to 128-fold overexpression. 60% of all tumors analyzed showed elevated levels of c-erbB-2 mRNA. |
| c-erbB-2 | lung | 1. Osaki et al., (1995) Chest 108(1):157–62: Lung tissue overexpression of c-erbB-2 was discovered in 42.5% of samples. 2. Lorenz et al., (1994) Clin. Invest. 72(2): 156–63: A 64-fold increase in the amount of c-erbB-2 mRNA was observed; 33% of lung tumors showed overexpression of c-erbB-2. |
| c-erbB-2 | ovarian | 1. Katsaros et al., (1995) Anticancer Res. 15(4):1501–10: Abnormally high expression of c-erbB-2 was found in 31% of tumor samples. 2. Felip et al., (1995) Cancer 75(8):2147–52: 21.7% of ovarian tumors showed overexpression of c-erbB-2. 3. Fan et al., (1994) Chin. Med. J. 107(8):589–93: c-erbB-2 amplification was found in 30.8% (8 of 26) of human ovarian cancers. 4. |

TABLE 1-continued

Representative List of Target Proto-Oncogenes

| Proto Oncogene | Tumor | Comments/References |
|---|---|---|
| | | vanDam et al., (1994) J. of Clin. Path. 47(10):914–9: 24% of ovarian tumors showed c-erbB-2 overexpression. 5. Csokay et al., (1993) Eur. J. of Surg. Oncology 19(6):593–9: c-erbB-2 amplification was found in 34% of fresh ovarian tumor samples. 6. McKenzie et al., (1993) Cancer 71(12):3942–5: 30% of ovarian tumor samples indicated c-erbB-2 overexpression. 7. Hung et al., (1992) Cancer Letters 61(2):95–103: A 100-fold c-erbB-2 overexpression was discovered in one human cell line. Two to four-fold amplification was also discovered. |
| mdm-2 | leukemia | Mdm-2 is the murine double minute-2 oncogene. 1. Bueso-Ramos et al., (1993) Blood 82(9):2617–23: 53% of cases showed overexpression of mdm-2 mRNA. The level of mdm-2 mRNA overexpression in some cases of leukemias was comparable to that observed in some sarcomas, which demonstrate more than 50-fold mdm-2 gene amplification. No evidence of gene amplification was observed. 2. Watanabe et al., (1994) Blood 84(9):3 158–65: 28% of patients with B-cell chronic lymphocytic leukemia or non-Hodgkin's lymphoma had 10-fold higher levels of mdm-2 gene expression. Mdm-2 over-expression was found more frequently in patients at advanced clinical stages. |
| c-myb | colon | V-myb is the oncogene of the avian myelo-blastoma virus. 1. Ramsay et al., (1992) Cell Growth and Diff 3(10):723–30: c-myb levels were always higher in colon cancer samples than normal tissue. 2. Alitalo et al., (1984) Proc. Natl. Acad. Sci. 81(14):4534–8: c-myb levels were always higher in colon cancer samples than normal tissue. |
| c-myc | breast | V-myc is the oncogene of the avian myelocytoma virus. 1. Lonn et al., (1995) Cancer 75(11):2681–7: Amplification of c-myb occurs in 16% of patients with breast cancer. 2. Hehir et al., (1993) J. of Surg. Oncology 54(4):207–9: myc overexpression was found in 60% of breast carcinoma samples. 3. Kreipe et al., (1993) Cancer Research 53(8):1956–61: Amplification of c-myc was found in 52.6% of samples that displayed a Ki-S1 labelling index exceeding 30%. 4. Watson et al., (1993) J. Nat. Cancer Inst. 85(11):902–7: Amplification of c-myc occurs in up to 20–30% of breast cancers. 5. Berns et al., (1992) Cancer Research 52(5):1107–13: Amplification was found in 20% of primary breast cancer patients; the range was 3–14 gene copies. 6. Watanabe et al., (1992) Cancer Research 52(19):5178–82: Expression of c-myc was increased by 10-fold. |
| c-myc | gastric/ colorectal | 1. Rigas, (1990) Clin. Gastroent. 12(5):494–9: Overexpression of c-myc is found in 80 of colon cancers. 2. Erisman et al., (1988) Oncogene 2(4):367–78: Adenocarcinoma cell lines express 5-10-fold elevated levels of c-myc mRNA. Eight to thirty-seven-fold higher levels of c-myc protein was found in tumor cell lines compared to normal cells. 3. Sikora et al., (1987) Cancer 59(7):1289–95: Up to 32-fold overexpression of c-myc mRNA was observed in 12 to 15 tumors. 4. Tsuboi et al., (1987) Biochem. and Biophys. Res. Comm. 146(2):705–10: Gastric Cancer: A 2-3-fold overexpression was observed in gastric cancer. A 2-10-fold overexpression was observed in colorectal cancer. |
| c-myc | lung | 1. Lorenz et al., (1994) Clin. Invest. 72(2):156–63: A 57-fold increase in c-myc mRNA levels was observed. 23% of samples indicated strong expression of c-myc. 2. Kato et al., (1993) Jap. J. of Cancer Res. 84(4):355–9: Liver tissue metastases from human small cell lung carcinoma revealed 30-fold amplification of c-myc. |
| c-myc | naso-pharn-geal | Porter et al., (1994) Acta Oto-Laryng. 114(1): 1105–9: 22% of samples showed intense staining for c-myc. |
| c-myc | ovarian | 1. Bian et al., (1995) Chin. J of Ob. Gyn. 30(7):406–9: 50% of samples showed amplification of c-myc. 2. Katsaros et al., (1995) Anticancer Res. 15(4):1501–10: 26% of samples exhibited c-myc amplification. 3. van Dam et al., (1994) J. Clin. Path. 47(10):914–9: Overexpression of c-myc was found in 35% of ovarian carcinomas. 4. Xin et al., (1993) Chin. J. of Ob. Gyn. 28(7):405–7: 54.5% of samples showed amplification of c-myc. 5. Tashiro et al., (1992) Int. J. of Cancer 50(5):828–33: Overexpression was found in 63.5% of all serous adenocarcinoma tissues and 37.3% of all ovarian carcinoma tissues. Significant overexpression of c-myc was observed at Stage III compared with other stages. |
| c-myc | prostate | Nag et al., (1989) Prostate 15(2):115–22: A 10-fold amplification of c-myc was observed. Fifty-fold higher levels of mRNA transcripts of c-myc were found. |
| c-ras | lung | Ras oncogenes were first recognized as the transforming genes of Harvey and Kirsten murine sarcoma viruses. Lorenz et al., (1994) Clin. Invest. 72(2):156–63: a 13-fold increase in overexpression of c-Ki-ras was observed. 18% of tumors displayed strong overexpression of c-Ki-ras. |
| c-ras | ovarian | 1. Katsaros et al., (1995) Anticancer Res. 15(4): 1501–10: Higher levels of ras protein than in normal or benign ovarian tumors were found in 45% of tumor samples. 2. vanDam et al., (1994) J. of Clin. Path. 47(10):914–9: 20% of ovarian tumors exhibited c-ras overexpression. The levels of expression of c-ras were much higher in tumors of patients with recurrent or persistent disease after chemotherapy, than in the tumors of patients at initial presentation. |
| c-src | breast | V-src is the oncogene of the Rous sarcoma virus, which induces sarcomas in chickens. Muthuswamy et al., (1994) Mol. and Cell. Biol 14(1):735–43: c-erbB-2-induced mammary tumors possessed 6-8-fold higher c-src kinase activity than adjacent epithelium. |
| c-src | colon/ colorectal | 1. Cartwright et al., (1994) J. of Clin. Invest. 93(2):509–15: c-src activity is 6-10-fold higher in mildly dysplastic ulcerative colitis (a chromic inflammatory disease of the colon with a high on incidence of colon cancer) than in non-dysplastic epithelia. This data suggests that activation of c-src is an early event in the genesis of UC colon cancer. 2. Talamonti et al., (1993) J. of Clin. Invest. 91(1):53–60: High level of c-src activity from colorectal cancer is found in liver metastases. 3. Termuhlen et al., (1993) J. of Surg. Res. 54(4):293–8: Colon carcinoma metastases to the liver had significantly increased activity of c-src with an average 2.2-fold increase. Extra-hepatic colorectal metastases demonstrated an average 12.7-fold increase in c-src activity over normal mucosa. |
| c-yes | colon | V-yes is the oncogene of two avian sarcoma viruses, Esh sarcoma virus and Y73. 1. Pena et al., (1995) Gastroent. 108(1):117–24: Twelve to fourteen-fold higher expression of c-yes was found in colonic transforming oncogene adenomas compared to normal mucosa. Activity of c-yes was elevated in adenomas that are at greatest risk for developing cancer. 2. Park et al., (1993) Oncogene 8(10):2627–35: A ten to 20-fold |

TABLE 1-continued

Representative List of Target Proto-Oncogenes

| Proto Oncogene | Tumor | Comments/References |
|---|---|---|
| | | higher than normal activity of c-yes was observed in 3 out of 5 colon carcinoma cell lines. A 5-fold higher than normal activity was found in 10 out of 21 primary colon cancers, compared to normal colonic cells. |

Selection of Cognate Transgene for Preparation of Cellular Immunogen

According to the present invention, a transgene construct is engineered comprising a transgene which is cognate to the target proto-oncogene (hereinafter "cognate transgene" or "CTG"). The transgene is selected such that it encodes a gene product which induces host immunoreactivity to host self-determinants of the product of the target proto-oncogene. The transgene should be expressed to very high levels in the transfectants. Thus, the construct should contain a strong promoter.

The product encoded by the cognate gene must have a high degree of sequence homology with the product of the target proto-oncogene, but also must display some amino acid differences with the target proto-oncogene product. Thus, there must be a subset of one or more amino acid differences between the target proto-oncogene and its cognate in order to provide immunogenic stimulus. Two classes of genes that satisfy these criteria are retroviral oncogenes and xenogenic proto-oncogenes. The word "xenogenic" is intended to have its normal biological meaning, that is, a property or characteristic referring or relating to a different species. Thus, a xenogenic proto-oncogene is meant to include the a homologous proto-oncogene of a species other than the host organism species. It may be appreciated that in the case of a target proto-oncogene, e.g. mdm-2, for which no retroviral homolog is yet known, a xenogenic homologue is advantageously utilized as the source of the DNA for the cognate transgene.

In principle, a more effective immunogenic stimulus would depend on the particular sequence, and not on the distinction between a retroviral oncogene and a xenogenic proto-oncogene in terms of their relative transforming capacity. Thus, in certain cases, a retroviral oncogene may be better at providing a tolerance-breaking immunogenic stimulus, and in other cases, a xenogenic proto-oncogene may be more effective. Example 1, herein, provides an illustration of the breaking of tolerance by the use of a retroviral oncogene. Example 4 provides an illustration of tolerance breaking by use of a xenogenic proto-oncogene.

The retroviral oncogene or xenogenic proto-oncogene DNA forming the CTG may comprise the wild type oncogene or proto-oncogene DNA. More preferably, a mutant DNA is utilized, which is engineered so as to be nontransforming in the host. The DNA is mutated to include one or more nucleotide insertions, deletions or substitutions which will encode an oncogene product which is nontransforming in the host, but retains the requisite degree of sequence homology with respect to the target proto-oncogene. A cognate transgene deletion mutant (hereinafter "dCTG") is preferred.

A protein sequence is generally considered "cognate" with respect to the target proto-oncogene-encoded protein if it is evolutionarily and functionally related between species. A more precise view of cognation is based upon the following sequence comparison carried out utilizing the FASTA program of Pearson and Lipman, *Proc. Natl. Acad. Sci. USA* (1988), 85:2444–2448, the entire disclosure of which is incorporated herein by reference. Cognation is attained upon satisfying two criteria imposed by FASTA; (i) alignment of segments corresponding to at least 75% of the target proto-oncogene's encoded amino acid sequence; (ii) at least 80% amino acid identity within the aligned sequences. The segments of the target proto-oncogene protein sequence and protein test sequence satisfying the two criteria are referred to as "homology regions". Accordingly, at least 75% of the target proto-oncogene protein sequence is alignable with the test sequence. The alignable segments or homology regions may, however, represent less than 75% of the total test polypeptide chain for the case of test sequences that may significantly exceed the target proto-oncogene protein in length.

One skilled in the art, armed with the FASTA program, may survey existing sequence data bases (either protein sequences or DNA sequences, insofar as the amino acid sequence is determined by FASTA for all reading frames) for test sequences which are cognate with respect to the target proto-oncogene. At the same time, one can isolate and then sequence what are very likely to be cognate test sequences (e.g. feline mdm-2, as likely to be cognate to human mdm-2) and use FASTA to verify the presumed cognation, according to the criteria set forth above. One may obtain the sequences of presumptive cognate proto-oncogenes from a large number of mammalian sequences and screen these sequences with FASTA according to the aforesaid formulation of cognation.

Because the product encoded by a CTG differs at a small number of amino acid positions from the product encoded by the target proto-oncogene, an immunogenic stimulus is provided that (i) is directed against the foreign protein and (ii) with a lower probability, induce an anti-self response. The CTG is selected such that the gene product will yield the greatest immunogenic stimulus to induce anti-self reactivity. Provided that overall sequence homology (preferably greater than about 75%) is maintained, the presence of scattered amino acid differences is desired, since any one residue would likely have a relatively low probability of inducing self-reactivity. Moreover, the greatest number of residue differences would be advantageous, consistent with maintaining the requisite degree of general sequence homology.

The selection of amino acid modifications for the CTG may be facilitated by resort to available computer-based models used to identify immunogenic peptide fragments of polypeptides. These models could be employed to select CTGs which would possess the maximum number of immunogenic peptides for a given HLA haplotype.

Screening Procedure for CTG Selection

Notwithstanding the availability of computer-based algorithms which have some predictive value, it is desirable to design CTGs with resort to a screening procedure based on an actual experimental assay that can be HLA-haplotype specific. Accordingly, cells are biopsied from a normal volunteer of particular haplotype. The cells are transfected with a CTG construct, preferably a dCTG construct, satisfying the criteria set for cognition. More preferably, the cells are transfected with multiple dCTGs, preferably at least five dCTGs, satisfying the criteria for cognition. The at least five dCTGs are selected to display amino acid differences that essentially extend throughout the polypeptide chains of the encoded sequences. The transfected cells are then used to immunize the volunteer in accordance with the immunization method of the present invention. After immunization, the human subject is tested in a standard delayed hypersensitivity (DH) reaction with $10^4$–$10^6$ irradiated, autologous fibroblasts, as transfected with the same dCTG (or series of dCTGs) as used for the immunizing preparation. A positive DH reaction (induration) would verify the induction of reactivity. The induction of reactivity in this assay is readily demonstrable because of the priming to the non-self determinants on the dCTG-encoded protein and the readout in the DH reaction of the same nonself determinants. Once DH reactivity is demonstrated in a DH reaction that directly tests the antigenicity of the non-self determinants encoded by the dCTG (i.e., priming with a non-self construct, DH testing with the same non-self construct), the subject can be then tested in a DH reaction based on testing with the autologous cells transfected with a dCTG derived from the human proto-oncogene itself (i.e., priming with a non-self construct, testing with the human self construct). Testing of a battery of human volunteers will lead to a catalogue of HLA-matched dCTGs, such that, for individuals of the same HLA haplotype, the use of the particular dCTG would be inductive of reactivity to proto-oncogene-encoded self. Different CTGs may thus be tested so as to correlate maximal secondary stimulation with a particular HLA haplotype.

At the same time, this procedure may be used with patients undergoing tumor resection (if post-operative immuno-suppressive protocols are not mandatory), such that prior to resection, a course of immunization would have been initiated, the endpoint of which would represent the development of a DH reaction.

Any given amino acid difference between the CTG-encoded product and the proto-oncogene-encoded product has a low probability of being a "tolerance-breaker". Thus, it is preferable to transfect the host cells with a mixture of multiple different CTGs, preferably dCTGs. The number of different dCTGs is preferably five or more. Moreover, it is preferred that, among themselves, the multiple dCTGs show amino acid differences that essentially extend throughout the polypeptide chains of the encoded sequences. The dCTGs would be selected to maximize amino acid differences and, at the same time, make sure that differences are found all along the polypeptide chain. It would thus not be preferable to select a battery of deletions all from within the same domain of the polypeptide chain.

According to a protocol which utilizes $10^7$ irradiated cells for immunization containing five separate dCTGs, five groups of $2\times10^6$ cells are included in one inoculate, each group of $2\times10^6$ having been transfected with a separate dCTG from the total set of five CTGs that are cognate to a particular proto-oncogene.

Selection of Non-Transforming Cognate Transgenes

Non-transforming cognate transgene variants are most advantageously derived via deletion of a sequence essential for transformation. Unlike point mutations which are potentially reversible due to back mutations, deletion mutations are irreversible. Furthermore, deletion mutations do not possess the inherent disadvantage attaching to point mutations, namely, even though the requirement for generation of an acceptable cognate transgene is for a qualitative difference with the wild type, i.e., non-transforming versus transforming, any given point mutation may be neutral or else quantitative in its effect, that is, the mutation may reduce but not totally eliminate transformability. Thus, according to a preferred embodiment of the invention, a deletion is created in a region of the cognate transgene which encodes an amino acid sequence required for transformation. Consonant with non-transformability, the smallest deletion possible so as to leave intact the bulk of the antigenicity of the transgene product is selected.

The engineering of a cognate transgene deletion mutant that satisfies these criteria is facilitated by reports of structure-function relationship in oncogene-encoded proteins. Such reports serve to identify regions of oncoproteins that are essential for transformation, as opposed to regions which are either neutral or serve merely to modulate transformability. Although such reports are usually based on in vitro transformation assays, and are therefore independent of immune effects, these studies can be exploited to aid in the construction of non-transforming dCTGs for use in the practice of the present invention.

The deletion mutant is engineered to include at least a part of the region identified as critical for transformation. In those cases where essential amino acids have been identified, the deletion will span these residues. The engineering of any desired deletion can be readily accomplished by polymerase chain reaction (PCR) according to conventional PCR techniques, based upon the known nucleotide sequence of the unmutated cognate transgene.

The following describes a representative protocol for deriving a non-transforming dCTG of the smallest possible deletion, for use in the practice of the present invention. A test dCTG, engineered on the basis of known or ascertained transformation-specific domains, and driven by the strongest possible promoter, is used to transfect murine 3T3 cells. A sister culture of 3T3 cells is also transfected, with non-deleted CTG. Each CTG or dCTG cell culture is inoculated into nude mice, in the absence of any treatment to render the cells non-dividing. Those dCTGs which do not yield tumors in the mice even after prolonged observation are then utilized as transgenes for the biopsied human cells which, upon transfection with the transgene, will serve as a cellular vaccine according to the practice of the present invention. The dCTGs are selected with the smallest deletion mutant consonant with non-transformability.

Some CTGs representing xenogenic proto-oncogenes may not be tumorigenic in the 3T3/nude mouse assay. For any such non-transforming CTG, it is not essential to generate a dCTG. However, even given non-tumorigenicity in nude mice, it may be desirable to opt for generation of a deletion mutant when the transgene is based upon a xenogenic proto-oncogene. In such cases, the deletion would be engineered so as to remove the homologous region to that deleted in the particular dCTG that corresponds to the deletion in the corresponding retroviral oncogene dCTG.

Even though the transgene construct may comprise mutant oncogene or proto-oncogene DNA which is nontransforming, it is nevertheless preferable, as a safety measure, to treat the transfected cells to render them non-dividing before inoculation back into the host. The cells are irradiated with a radiation dosage sufficient to render them non-dividing.

Oncogenicity Assay of Cognate Transgenes

As a further safety measure, the oncogenicity of a given dCTG is preferably thoroughly tested prior to infection of the human host cells which are used as cellular immunogens according to the practice of the present invention. For example, an oncogenicity testing regimen may take the form of three separate assays: (i) dCTG transfection of NIH 3T cells, followed by inoculation into nude mice; (ii) dCTG transfection of human fibroblasts, followed by inoculation into nude mice; and (iii) dCTG transfection of human fibroblasts, followed by an in vitro test of anchorage-dependent growth. In principle, all three should be negative to validate the use of any given dCTG in the vaccination method of the present invention.

According to the oncogenicity assay (i), after stable transfection of NIH 3T3 cells with the test dCTG, the transfectants are inoculated into nude mice. Tumorigenicity of the transfectants in the mice is then evaluated according to standard protocols.

According to oncogenicity assay (ii), human fibroblasts are transfected with the test dCTG as proposed in the above human immunization protocol. After stable dCTG transfection of human fibroblasts, however, rather than carrying out X-irradiation of the transfectants to render them non-dividing, followed by inoculation of the irradiated transfectants back into the human host, the transfectants are directly inoculated into nude mice as a direct test of tumorigenicity. Given the greater susceptibility of murine 3T3 cells to oncogenic transformation, vis a vis primary human or murine transfectants fibroblasts, assay (ii) is probably much less sensitive than assay (i), but does have the advantage of offering a direct test of dCTG oncogenicity in human cells.

According to oncogenicity assay (iii), non-irradiated dCTG-transfected human fibroblasts are assayed for anchorage-dependent growth, i.e. colony formation in soft agar, as a test of dCTG transforming potential in human cells. Anchorage independence, as defined by the ability of cells to grow whe9 n suspended in semisolid medium, is a common phenotype acquired by human tumor cells, particularly those tumor cells of mesenchymal origin, such as fibrosarcomas. While assay (iii) has no in vivo readout, it offers an independent test of the critical issue of dCTG oncogenicity in human cells.

The oncogenicity assays are performed according to published protocols. Assay (i), comprising dCTG transfection of NIH 3T3 cells followed by inoculation into nude mice, may be performed according to the protocol of Stevens et al., Proc. Natl. Acad. Sci. USA (1988), 85:3875–3879, including DNA transfection by the calcium phosphate coprecipitation method of Manohaven et al., Carcinogenesis (1985), 6:1295–1301. Accordingly. NIH 3T3 cells ($7.5 \times 10^5$ cells per 100-mm dish) are exposed to a calcium phosphate-DNA coprecipitate (40 µg of genomic DNA plus 3 µg of pSV2neo per dish) for 4 hours. Two days later, each dish is trypsinized and reseeded into a 175-cm$^2$ flask. For the next 10 days, cultures are selected in G418 (400 µg/ml), and the flasks are then trypsinized and cells are replated in the same flask to disperse the G418-resistant colonies into a diffuse lawn of cells. Two days later, the cells are harvested and washed with serum-free medium prior to injection. One injection of $5 \times 10^6$ cells into the right flank and one injection of $1 \times 10^7$ cells into the left flank, each in a volume of 200 µl, are done on each nude mouse. Injection sites are monitored at 3- or 4-day intervals for 100 days. The sites are scored for the number of tumors induced per injection site.

Oncogenicity assay (ii), whereby dCTG transfection of human fibroblasts followed by inoculation into nude mice, is carried out in the same manner as assay (i) except that for assay (ii) the human fibroblast transfectants are substituted for the murine 3T3 transfectants.

Assay (iii), involves a test of the in vitro anchorage-dependent growth of dCTG-transfected human fibroblasts. The assay is carried out as described in Stevens et al., J. Cancer Res. and Clin. Oncol. 1989, 115:118–128. $1 \times 10^5$ cells are seeded per 60-mm dish into 0.33% Noble agar over a 6-ml 0.5% agar base layer in Hams F10 supplemented with 6% fetal bovine serum. A portion of the agar suspension is diluted with Hams F10 plus 6% fetal calf serum to 200 cells/5 ml to determine the cloning efficiency of these cells when seeded into plastic 60-mm dishes. Agar dishes are fed with 1 ml Hams F10 supplemented with 6% fetal bovine serum on the 1st and 15th day after seeding. Four weeks after seeding, all agar colonies >75 µm in diameter are counted and the colony counts are normalized to the plating efficiencies which aliquots of the initially seeded cells showed on plastic. This comparison, or normalization, of the agar colony counts to the plastic dish colony counts is useful in identifying and correcting for any mechanical artifacts which might result from the seeding into agar of dead cells that had persisted from the initial transfection treatment or from heat-induced cell death, which might have occurred while suspending cells in molten agar during the process of seeding the agar dishes.

The following is a partial list of various deletions which, based upon published accounts of experiments with human or animal cells, are believed to render the identified CTG non-tumorigenic.

TABLE 2

Deletion Mutations Rendering Indicated Gene Non-Transforming

| CTG | Genbank accession number for sequence | Number of amino acids in gene | Amino acids deleted, rendering CTG non-transforming | References |
|---|---|---|---|---|
| Akz-2 (c-akt) (mouse) | M95936; SEQ ID NO:3 (Mus musculus serine/threonine kinase) | 480 | 148–234 | Bellacosa et al., Science (1991), 254:274–278; Bellacosa et al., Oncogene (1993), 8(3):745–54. |
| c-neu (c-erbB-2) (rat) | M11730; SEQ ID NO:4 (human tyrosine kinase-type receptor (HER2) gene | 1255 | 1–731 | Bargmann et al., EMBO (1988), 7(7):2043–52; Bernards et al., Proc. Natl. Acad. Sci. USA (1987), 84(19):6854–8. |
| mdm-2 (human) | U33199; SEQ ID NO:5 (human mdm-2-A mRNA); U33200; SEQ ID NO:6 (human mdm-2-B mRNA); U33201; SEQ ID NO:7 (human mdm-2-C mRNA); U33202; SEQ ID NO:8 (human mdm-2-D | 489 | 9–155 | Dubs-Poterszman, Oncogene (1995), 11(11):2445–50. |
| c-myb (human) | J02012; SEQ ID NO:10 (proviral oncogene v-myb) | 640 | 275–327 | Kalkbrenner et al., Oncogene (1990), 5(5):657–61. |

TABLE 2-continued

Deletion Mutations Rendering Indicated Gene Non-Transforming

| CTG | Genbank accession number for sequence | Number of amino acids in gene | Amino acids deleted, rendering CTG non-transforming | References |
|---|---|---|---|---|
| c-myc (human) | X00364; SEQ ID NO:11 (human c-myc oncogene) | 439 | 129–144 | Sarid et al., Proc. Natl. Acad. Sci. USA (1987), 84(1):170–3. |
| v-ras (Harvey Murine Sarcoma Virus) | M77193; SEQ ID NO:12 (Rat sarcoma virus v-ras oncogene) | 189 | 3244 | Zhang et al., Science (1990), 249: 162–5 (1990) |
| v-src (Rous Sarcoma Virus) | U41728; SEQ ID NO:13 (RSV Schmidt-Ruppin A clone SRA-V; v-src gene) | 526 | 430–433 | Bryant et al., Mol. Cell. Bio. (1984), 4(5):862–6. |
| c-yes (chicken) | D00333; SEQ ID NO:14 (human c-yes-2 gene) | 541 | 438–441 | Zheng et al.; Oncogene (1989), 4(1):99–104. |

Engineering of Vectors for Host Cell Transfection

The engineering of vectors for expression of a particular CTG, preferably a dCTG, is based on standard methods of recombinant DNA technology, i.e. insertion of the dCTG via the polylinker of standard or commercially available expression vectors. The dCTG is operably linked to a strong promoter. Generally speaking, a "strong" promoter is a promoter which achieves constitutively high expression of the dCTG in the transfected cells. Each promoter should include all of the signals necessary for initiating transcription of the relevant downstream sequence. These conditions are fulfilled, for example, by the pBK-CMV expression vector available from Stratagene Cloning Systems, La Jolla, Calif. (catalog no. 212209). The pBK-CMV vector contains the cytomegalovirus (CMV) immediate early promoter. dCTGs xenogenic with respect to a particular target proto-oncogene may be isolated by conventional nucleic acid probing techniques, given the availability of a highly homologous probe represented by the cognate retroviral oncogene and/or the human proto-oncogene itself.

Collection of Host Cells for Transfection

The host cells which may be transfected to derive the cellular immunogens of the present invention must express class I MHC and be susceptible to isolation and culture. Fibroblasts express class I MHC and may be cultured. Other preferred host cells are bone marrow-derived antigen-presenting cells such as macrophages, follicular dendritic cells, and Langerhans cells, for example.

Primary skin fibroblasts may be obtained as follows. Accordingly, punch biopsies of host human skin are performed to harvest fibroblasts. Punch biopsies can be performed by a competent physician as a standard clinical procedure. Each biopsy yields a starting population of $1-2 \times 10^7$ cells that would proliferate in culture. Methods for the preparation of tissue cultures of human fibroblasts are well developed and widely used. See, Cristofalo and Carpenter, J. Tissue Culture Methods (1980), 6:117–121, the entire disclosure of which is incorporated herein by reference. Essentially, skin obtained by punch biopsy is washed using an appropriate wash medium, finely minced and cultured in a suitable culture medium, such as Dulbecco's Modified Eagle Medium (DMEM), under $CO_2$ at 37° C. The cells are trypsinized with a trypsin solution and transferred to a larger vessel and incubated at 37° C. in culture fluid.

Host Cell Transfection

The expression vector carrying the dCTG is used to transfect biopsied host cells according to conventional transfection methods. One method of transfection involves the addition of DEAE-dextran to increase the uptake of the naked DNA molecules by a recipient cell. See McCutchin and Pagano, J. Natl. Cancer Inst. (1968) 41:351–7. Another method of transfection is the calcium phosphate precipitation technique which depends upon the addition of $Ca^{++}$ to a phosphate-containing DNA solution. The resulting precipitate apparently includes DNA in association with calcium phosphate crystals. These crystals settle onto a cell monolayer; the resulting apposition of crystals and cell surface appears to lead to uptake of the DNA. A small proportion of the DNA taken up becomes expressed in a transfectant, as well as in its clonal descendants. See Graham et al., Virology (1973), 52:456–467 and Virology (1974), 54:536–539.

Preferably, transfection is carried out by cationic phospholipid-mediated delivery. In particular, polycationic liposomes can be formed from N-[1-(2,3-dioleyloxy) propyl]-N,N,N-trimethylammonium chloride (DOTMA) or related liposome-forming materials. See Felgner et al., Proc. Natl. Acad. Sci. USA (1987) 84:7413–7417 (DNA-transfection); Malone et al., Proc. Natl. Acad. Sci. USA (1989), 86:6077–6081) (RNA-transfection). One preferred technique utilizes the LipofectAMINE™ Reagent (Cat. No. 18324-012, Life Technologies, Inc., Gaithersburg, Md.) which is a 3:1 (w/w) liposome formulation of the polycationic lipid 2,3-dioleyloxy-N-[2(spermiinecarboxamido) ethyl-N,N-dimethyl -1-propanaminium trifluoroacetate (DOSPA) (Chemical Abstracts Registry name: N-[2-({2,5-bis[(3-aminopropyl)amino]-1-oxypentyl}amino)ethyl]-N, N-dimethyl -2,3-bis(9-octadecenyloxy)-1-propanaminium trifluoroacetate), and the neutral lipid dioleoyl phosphatidylethanolamine (DOPE) in membrane filtered water. Transfection utilizing the LipofectAMINE™ Reagent is carried out according to the manufacturer's published protocol. The protocol (for Cat. No. 18324-012) provides for either transient or stable transfection, as desired.

The advantage of transient expression is its rapidity, i.e. there is no requirement for cellular proliferation to select for stable integration events. This rapidity could conceivably be of major clinical importance, in cases of an already metastatic tumor burden, wherein the weeks required for selection of stable transfectants may simply not be available to the clinician.

There are, nonetheless, two general disadvantages to the use of transient transfection. The first is that expression usually peters out after a few days, in contrast to the continual expression in the case of stable transfection. This is not particularly crippling in terms of our immunization protocol. The inoculated, irradiated cells used for immunization would likely not survive in vivo for more than 4 or 5 days, in any case. Thus the nominal advantage accruing to stable transfection, that of a long-duration expression by the progeny of the parental inoculated cell, is not of particular relevance in the case of the immunizing regime described herein, which is based on the use of non-dividing, probably short-lived cells.

A second disadvantage of transient transfection resides in the fact that it yields a cell population, only a subset of which has actually been transfected and thus expresses the protein encoded by the transgene. This problem is obviated in the case of stable transfection, wherein over time one can develop a pure population of transfectants via selection for a resistance marker, such as neo, under conditions of clonal proliferation of the initial stable transfectants, i.e. daughter cells of transiently transfected cells lack the transgene, in contrast to the case with stable transfectants. In the situation where there is sufficient time to effect immunization based on stably transfected cells, the progeny of all transfected clones would be utilized, not just the progeny of a single clone, as is sometimes done for detailed biochemical and molecular analyses of gene expression. Clearly the more clones utilized, the more quickly one can arrive at the requisite number of cells to be used for immunization.

Percentage of Cells Exhibiting dCTG Expression

The percentage of cells exhibiting dCTG expression may be determined by an immunohistology assay. In this procedure, a small number of cells (~500) from the harvested pellet following centrifugation of transfected cells are deposited on a cover slip and fixed with cold acetone. At this point, a standard immunohistological assay is carried out with the cells on the cover slip, i.e. addition of a primary monoclonal antibody reactive to the dCTG-encoded protein, followed by the addition of a developing antibody, e.g. a fluorescent tagged antibody reactive to the primary monoclonal antibody. Measurement of the percentage of cells scoring as dCTG-positive in the fluorescent assay allows a determination of the number of positive transfectants in the starting culture, and thus the number of total cells to be used for immunization to arrive at the desired number of dCTG-positive cells to be inoculated in the patient.

If, as would be almost certain, the percentage of cells scoring as dCTG-positive is less than one hundred percent, one can simply increase the number of cells to be used for immunization, so as to include the desired number of transfectants. The non-transfected cells in the immunizing population would simply represent x-irradiated, autologous fibroblasts that would constitute no danger to the patient.

Transfectant Irradiation

Prior to return to the host, the transfected cells are preferably irradiated. The transfectants are irradiated with a radiation dose sufficient to render them non-dividing, such as a dose of 25 By or 2500R. The cells are then counted by trypan blue exclusion, and about $2 \times 10^7$ irradiated transfectants are resuspended in a volume of 0.2–0.4 ml of Hanks Balanced Salt Solution.

Vaccination Procedure

The transfected cells are returned to the host to achieve vaccination. The cells may be reimplanted at the same body site from which they were originally harvested, or may be restored to a different site.

It is the object of the present invention to generate a systemic tumor immune response, so as to fight metastasis formation wherever any metastases are found. Accordingly, there is no reason to inject the transfected cells at the same body site from which they were taken. Intramuscular, intraperitoneal or subcutaneous inoculation at a distal site would suffice to yield a systemic response. Thus, patients are vaccinated with the transfected cells accordingly.

For s-crc overexpression associated with colon carcinoma, partial venous inoculation is preferred, as the liver is a frequent site of metastases. For vaccinating against breast cancers and lymphomas, systemic immunization is preferred.

As a general rule, it is desirable to generate the strongest immune response consistent with clinical monitoring of no adverse side effects, i.e. multiple rounds of inoculation with, for example $10^7$ cells, at each round. The number of rounds of inoculation is selected accordingly. The efficacy of the inoculation schedule may be monitored by a delayed hypersensitivity reaction administered to the patient. A course of about up to 10 inoculations, at 2–3 week intervals, may be utilized. It may be appreciated that the inoculation schedule may be modified in view of the immunologic response of the individual patient, as determined with resort to the delayed-type hypersensitivity (DTH) reaction.

Patient Response Monitoring by Delayed-type Hypersensitivity Reaction

Patients are assessed for reactivity to the irradiated transfectants by a test of skin reactivity in a DTH reaction. DTH has been used clinically (Chang et al. (1993), *Cancer Research* 53:1043–1050). To measure reactivity to the autologous irradiated transfectants, $10^4$–$10^6$ cells in a volume of 0.1 ml Hanks buffered saline solution (HBSS) are inoculated intradermally into the host. Induration is measured 48 hours later, as an average of two perpendicular diameters (responses of greater than $\geq 2$ mm is considered positive).

One advantage to the DTH assay is that it can independently assess the induction of T cell reactivity to (i) the transfectants used for immunization (i.e. the set of 5 or more dCTGs chosen for immunization purposes, each containing non-self determinants) and (ii) transfectants, as transfected with the human dCTG itself containing only self determinants. Thus, the induction of reactivity to the transfectants used for immunization establishes that the immunizing transfectants are in fact immunogenic, that is, the patient has not exhibiting a much weakened capacity for immune response. If the patient is demonstrably capable of response to the immunizing transfectants, then skin testing with the dCTG (human) transfectants would establish whether or not reactivity to the human proto-oncogene encoded product had been induced. According to the practice of the invention, inoculation of the immunizing transfectants would continue for at least as long as the induction of reactivity to the human proto-oncogene-encoded protein occurs.

The practice of the invention is illustrated by the following nonlimiting examples.

EXAMPLE 1

Immunization of Chickens Against c-src(527) Induced Tumors By Vaccination with v-src DNA A. Genes The oncogene c-src(527) is an activated form of chicken c-src. Its protein product $pp60^{c-src(527)}$ differs from the protein product of c-src, $pp60^{c-src}$, by only a single amino acid substitution, phenylalanine for tyrosine at residue 527 (Kmiecik and Shalloway, (1987) *Cell* 49, 65–73). This substitution eliminates the negative regulatory influence exerted on $pp60^{c-src}$ phosphokinase activity by the enzymatic phosphorylation of the position 527 tyrosine. The protein product of v-src, $pp60^{v-src}$, shows a number of sequence differences with $pp60^{c-src}$ (Takeya and Hanafusa, (1983) *Cell* 32, 881–890), including scattered single amino acid substitutions within the first 514 residues and a novel C terminus of 12 amino acids (residues 515–526), in place of the nineteen C terminal amino acids of $pp60^{c-src}$ (residues 515–533). Both the v-src-positive plasmid, pMvsrc, and the c-src(527)-positive plasmid, pcsrc527, were originally shown (Kmiecik and Shalloway, (1987) *Cell* 49, 65–73) to transform murine NIH 3T3 cells in culture. However, the v-src-induced transformants exhibited a more rapid or more extensive colony growth in soft agarose than the c-src(527)-induced transformants, as well as a usually shorter latency of tumor formation in nude mice (id.).

B. Plasmids 1. pvSRC-C1

The pVSRC-C1 plasmid was prepared as described by Halpern et al., (1991) *Virology* 180, 857–86. Essentially, the plasmid was derived from the pRL'-src plasmid (Halpern et al., (1990) *Virology* 175, 328–331) by subcloning the v-src (+) XhoI-EcoRI fragment of the latter into the multiple cloning sequence of pSP65 (Melton et al., (1984) Nucleic Acids Res. 12, 7035–7056) which had been cleaved with SalI and EcoRI; since ligation of the XhoI overhang at the SalI site destroys both recognition sequences, subsequent removal of the v-src(+) insert from the vector was achieved by digestion with EcoRI and with HindIII, which cleaves at a position in the multiple cloning sequence adjacent to the SalI site. The pVSRC-C1 plasmid was restricted with EcoRI and HindIII, so as to liberate the tumorigenic insert. This insert included the v-src oncogene of the subgroup A strain of Prague RSV, as flanked downstream by a portion of the long terminal repeat (LTR) of RSV (from the 5'to start of the LTR, to the single EcoRi site).

2. pMvsrc

The pMvsrc plasmid was generously provided by Dr. David Shalloway, Cornell University, Ithaca, N.Y. The plasmid is prepared according to Johnson et al., (1985) *Mol. Cell. Biol.* 5, 1073–1083. Briefly, the 3.1-kb BamHI-Bg/II Schmidt Ruppin A v-src fragment from plasmid pN4 (Iba et al., (1984) *Proc. Nat. Acad. Sci. USA* 81, 4424–4428) is inserted into the pEVX plasmid (Kriegler et al., (1984) *Cell* 38,483–491) at a Bg/II site lying between two Moloney murine leukemia virus (MoMLV) long terminal repeats (LTRs). This fragment contains 276 bp of pBR322 DNA from the pBR322 BamHI to SalI sites followed by 2.8 kb of Rous sarcoma virus (RSV) DNA from the SalI site that is about 750 bp upstream of the env termination codon down to the NruI site that is about 90 bp downstream of the v-src termination codon. (The NruI site is converted to a Bg/II site in the construction of pN4.) Ligation is performed by using a 10:1 insert-vector DNA fragment molar ratio.

The pMvsrc plasmid was restricted with NheI, so as to liberate a tumorigenic fragment. The fragment included the v-src oncogene of the subgroup A strain of Schmidt-Ruppin RSV, as flanked upstream by most of the Moloney murine leukemia virus (MoMLV) LTR (from the NheI site near the 5' start of the LTR, to the 3' end of this LTR) and downstream by a small portion of the MoMLV LTR (from the 5' start to the NheI site).

3. pcsrc527

The pcsrc527 plasmid is prepared according to Kmiecik and Shalloway, (1987) *Cell* 49, 65–73. Briefly, a plasmid is constructed by cleaving expression vector pEVX (Kriegler et al., (1984) *Cell* 38,483–491 at its unique BgIII site lying between two MoMLV LTRs and inserting the 3.2 kilobase (kb) pair BamHI-BgIII hybrid src fragment from plasmid pHB5 in the proper orientation. This fragment contains sequences from pBR322, the SRA env 3'region, SRA v-src, src from recovered ASV, and chicken c-src. The BgIII site is generated by insertion of a linker at the SacI site about 20 bp downstream from the c-src termination codon. The restriction map of pMHB5 contains the MoMLV splice donor about 60 bp downstream from the 3'end of the upstream LTR and the v-src splice acceptor about 75 bp upstream from the src ATG.

Plasmid pMHB5527 is constructed by inserting the synthetic double-stranded DNA oligomer

5'CCAGTTCCAGCCTGGAGAGAACCTATA (SEQ ID NO:1) 3'

3'TCGGGGTCAAGGTCGGACCTCTCTTGGATATCTAG (SEQ ID NO:2) 5' into pMHB5 between the BanII site at c-src codon 524 and the downstream unique BgIII site. This alters the TAC Tyr 527 codon to a TTC Phe codon while preserving the remaining c-src coding region. Equimolar amounts of the double-stranded oligomer and three gel-purified tandem restriction fragments from pMHB5 are ligated in one reaction, which contains the following: the oligomer with BanII and BgIII complementary ends, the 3 kb BgIII-BgII (BgII in the pEVX ampicillin resistance gene) partial digest fragment, the adjacent 6.1 kb BgII-BgII (downstream BgII in c-src) fragment, and the 0.38 kb BgII—BanII (BanII at c-src codon 524) fragment.

Plasmid pcsrc527 is constructed by replacing the 2 kb SalI (in env)-MluI (in c-src) fragment in plasmid pMHB5527, with the homologous fragment from plasmid p5H. This fragment contains the coding sequence for the c-src amino region (codons 1 to 257) that have been isolated by molecular cloning of a c-src provirus and previously shown by sequencing to contain authentic c-src sequence without the mutation at codon 63 (Levy et al., (1986) *Proc. Natl. Acad. Sci. USA* 83, 4228–4232). Equimolar amounts of complementary gel-purified SalI-MluI fragments from p5H and the other plasmids are ligated.

The pcsrc527 plasmid was restricted with NheI, so as to liberate a tumorigenic fragment. The tumorigenic fragment included the c-src(527) oncogene, as flanked by the same LTR complement as in pMvsrc.

C. Animals

Chickens of two closed lines, SC and TK, were utilized. These lines differ at the major histocompatibility (B) complex ($B^2/B^2$ for the SC line, $B^{15}/B^{21}$ for the TK line). Embryonated eggs were obtained from Hyline International (Dallas Center, Iowa). All chickens were hatched at the University of New Hampshire Poultry Research Farm and housed in isolation.

D. Tumor Induction by Plasmid DNA

Tumors were induced by subcutaneous inoculation in the wing web of a src-positive plasmid according to the technique described by Fung et al. (1983) *Proc. Natl. Acad. Sci. USA* 80, 353–357 and Halpern et al., (1990) *Virology* 175, 328–331. Of the three tumorigenic plasmids utilized here, all were adjusted, prior to inoculation, to a concentration of 100 µg of enzyme-restricted DNA per 100 µl of phosphate-buffered saline. The conditions of inoculation used for particular experiments (age of chicken at time of inoculation, amount of plasmid, etc.) are indicated below.

E. Growth of Primary (wing web) Tumors in TK or SC Chickens

Inoculated with pVSRC-C1, pMvsrc or pcsrc527

Individual 1-day-old chickens of line TK or of line SC were inoculated with 100 µg of either pVSRC-C1, pMvsrc or pcsrc527. The mean tumor diameter (mm) at a particular time point and for any one group of TK or SC line chickens inoculated with an individual src-positive construct was computed as the sum of the diameters of the primary tumors divided by the number of chickens surviving to that point. The results are shown in FIG. 1A (line TK) and FIG. 1B (line SC). The ratios at each time point show, for a particular group, the number of chickens bearing palpable tumors to the total number of survivors to that point (standard typeface for pcsrc527, italics for pVSRC-C1, bold typeface for pMVsrc). Error bars (unless obscured by the symbol) indicate standard error.

F. Growth of Challenge (wing web) Tumors in Test and Control Line TK Chickens Under Conditions of Priming and Homologous Challenge with pcsrc527 or Priming and Homologous Challenge with pVSRC-C1

Growth of challenge (wing web) tumors in test and control line TK chickens was determined under conditions of (i) priming and homologous challenge with pcsrc527, or (ii) priming and homologous challenge with pVSRC-C1. Test chickens were primed at 1 day posthatch with 100 µg of construct; test and control chickens were challenged at five weeks posthatch with 200 µg of construct. The mean challenge tumor diameter was computed as described in the preceding section. At each time point the ratio of chickens bearing palpable challenge tumors to total number of survivors to that point is indicated for priming and homologous challenge with pcsrc527 (FIG. 2A) and priming and homologous challenge with pVSRC-C1 (FIG. 2B) (standard typeface for control group, bold typeface for test group). The statistical comparison between the mean challenge tumor diameters of the test versus the control group at a particular time point was made using a two-tailed student's t test, *($p<0.05$), ($p<0.01$), *($p<0.001$). The statistical comparison between the ratios of chickens bearing palpable challenge tumors to total number of survivors of the test versus the control group at a particular time point was made using a chi-squared test; the paired ratios are underlined for only those time points where $p<0.05$. Error bars indicate standard error.

G. Growth of Challenge ( wing web) Tumors in Test and Control line TK chickens under Conditions of Priming with pVSRC-C1 and Heterologous Challenge with pcsrc527, or Priming with pcsrc527 and Heterologous Challenge with pVSRC-C1

Growth of challenge (wing web) tumors in test and control line TK chickens, was determined under conditions of (i) priming with PVSRC-C1 and heterologous challenge with pcsrc527, or (ii) priming with pcsrc527 and heterologous challenge with pVSRC-C1. Test chickens were primed at 1 day posthatch with 100 µg of construct; test and control chickens were challenged at five weeks posthatch with 200 µg of construct. The mean challenge tumor diameter was computed as described in Section E. At each time point the ratio of chickens bearing palpable challenge tumors to total number of survivors to that point is indicated for priming with pVSRC-C1 and heterologous challenge with pcsrc527 (FIG. 3A) and priming with pcsrc527 and heterologous challenge with pVSRC-C1 (FIG. 3B) (standard typeface for control group, bold typeface for test group). Statistical comparisons were made between test and control groups at a particular time point as de scribed in the preceding section [*($p<0.05$), ($p<0.01$), *($p<0.001$), for the student's t test], and the paired ratios are underlined for only those time points where, in the chi-squared test, $p<0.05$. Error bars indicate standard error.

H. Discussion

Figure 1B:
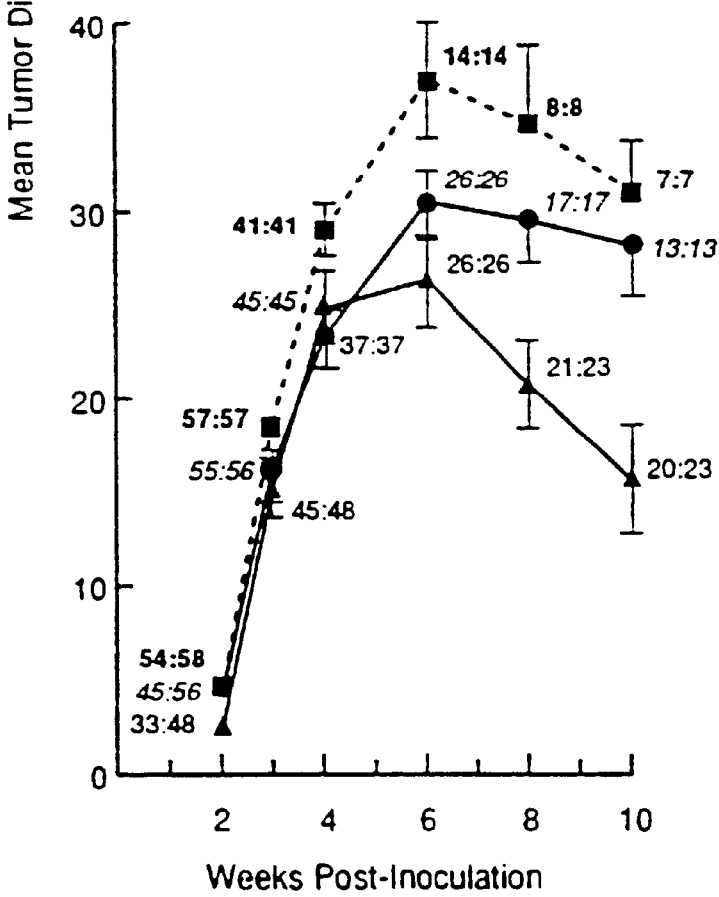

In a direct comparison of the growth of tumors induced in line TK by either pMvsrc or pVSRC-C1, a similar pattern of relatively rapid regression was observed. This result established that the difference in LTR complement between these two v-src positive constructs did not exert a major influence on the tumor growth pattern in the TK line (FIG. 1A). By contrast, much more extensive and persistent tumor growth resulted from inoculation of TK chickens with the pcsrc527 construct (FIG. 1A). The relatively greater growth capacity of tumors induced by this construct indicated that in the TK line, the c-src(527) oncogene is much more highly tumorigenic than the v-src oncogene. This difference did not, however, generalize to the SC line (FIG. 1B). The SC line was chosen for comparison with the TK line on the basis of earlier observations (Halpern et al., (1993) *Virology* 197, 480–484) that v-src DNA-induced tumors engender a much weaker tumor immune response in line SC than in line TK. Whereas the growth of pcsrc527-induced primary tumors was virtually indistinguishable in the two lines, the growth of the v-src-induced tumors was considerably greater in the SC than in the TK line (FIGS. 1A and 1B). Thus v-src, but not c-src(527), gives rise to primary tumors whose growth patterns differ in the two lines analyzed here.

Figure 2A:
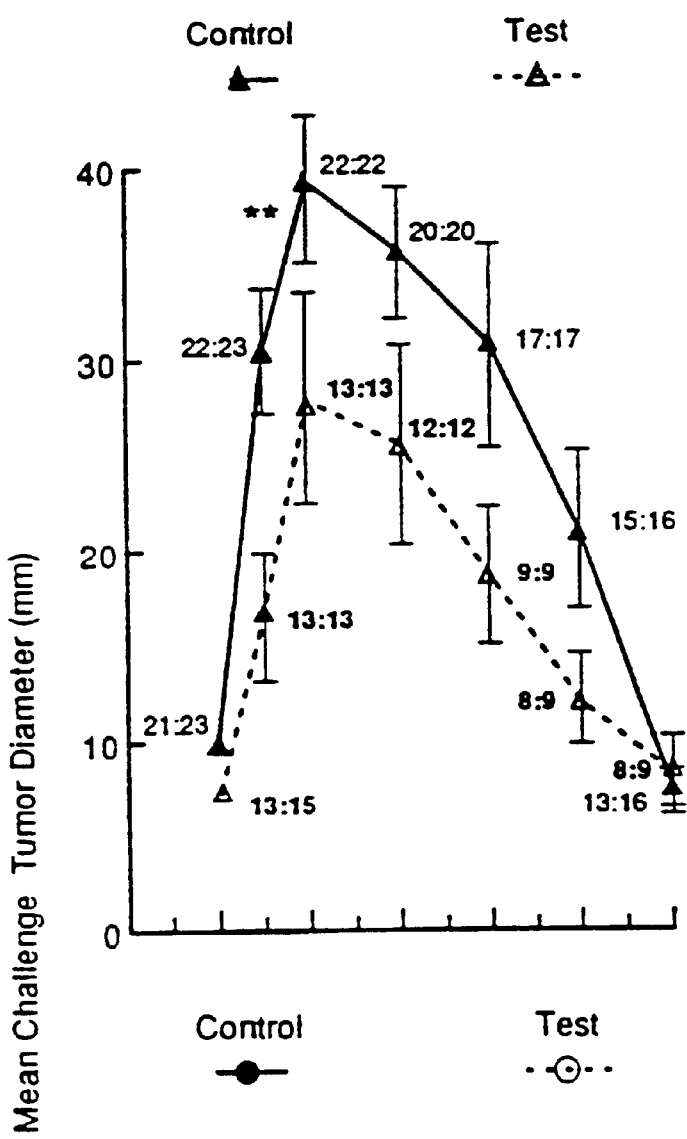
FIGS. 2A and 2B are plots of the growth of challenge (wing web) tumors in test and control line TK chickens under conditions of (i) priming and homologous challenge with plasmid pcsrc527 (FIG. 2A: —Δ—, test; —▲—, control), or (ii) priming and homologous challenge with plasmid pVSRC—C1 (FIG. 2B: —○—, test; —●—, control). Test chickens were primed at 1 day posthatch with 100 μg of construct; test and control chickens were challenged at five weeks posthatch with 200 μg of construct. The mean challenge diameter was computed as in FIGS. 1A and 1B. At each time point the ratio of chickens bearing palpable challenge tumors to total number of survivors to that point is indicated (standard typeface for control group, bold typeface for test group). The statistical comparison between the mean challenge tumor diameters of the test versus the control group at a particular time point was made using a two-tailed student's t test, *($p<0.05$), ($p<0.01$), * ($p<0.001$). The statistical comparison between the ratios of chickens bearing palpable challenge tumors to total number of survivors of the test versus the control group at a particular time point was made using a chi-squared test; the paired ratios are underlined for only those time points where $p<0.05$. Error bars indicate standard error.
Figure 2B:
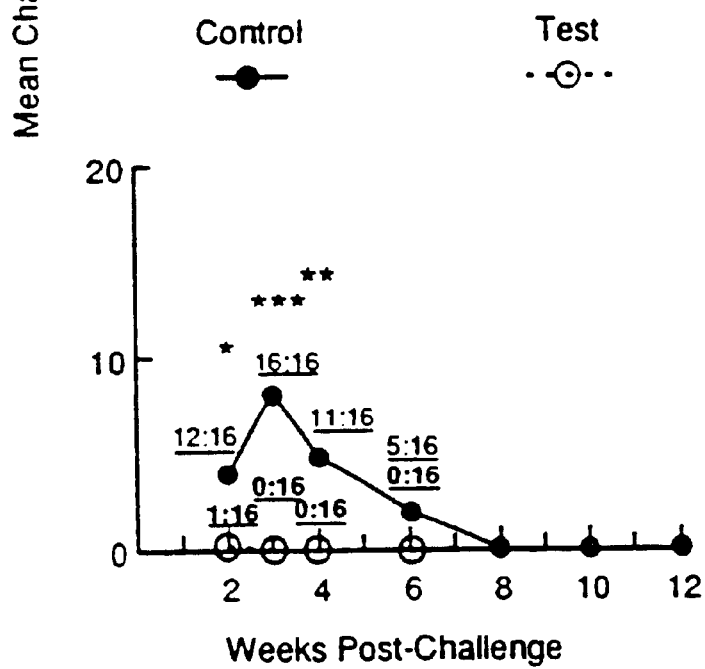

Only minimal protection against homologous challenge was observed under conditions of priming to c-src(527) DNA, indicative of the induction of a relatively weak tumor immune response (FIG. 2A; a statistically significant lowering of challenge tumor growth in the test versus the control chickens was observed at only one time point). By contrast, the v-src DNA-primed chickens showed excellent protection against the homologous tumor challenge (FIG. 2B).

Figure 3A:
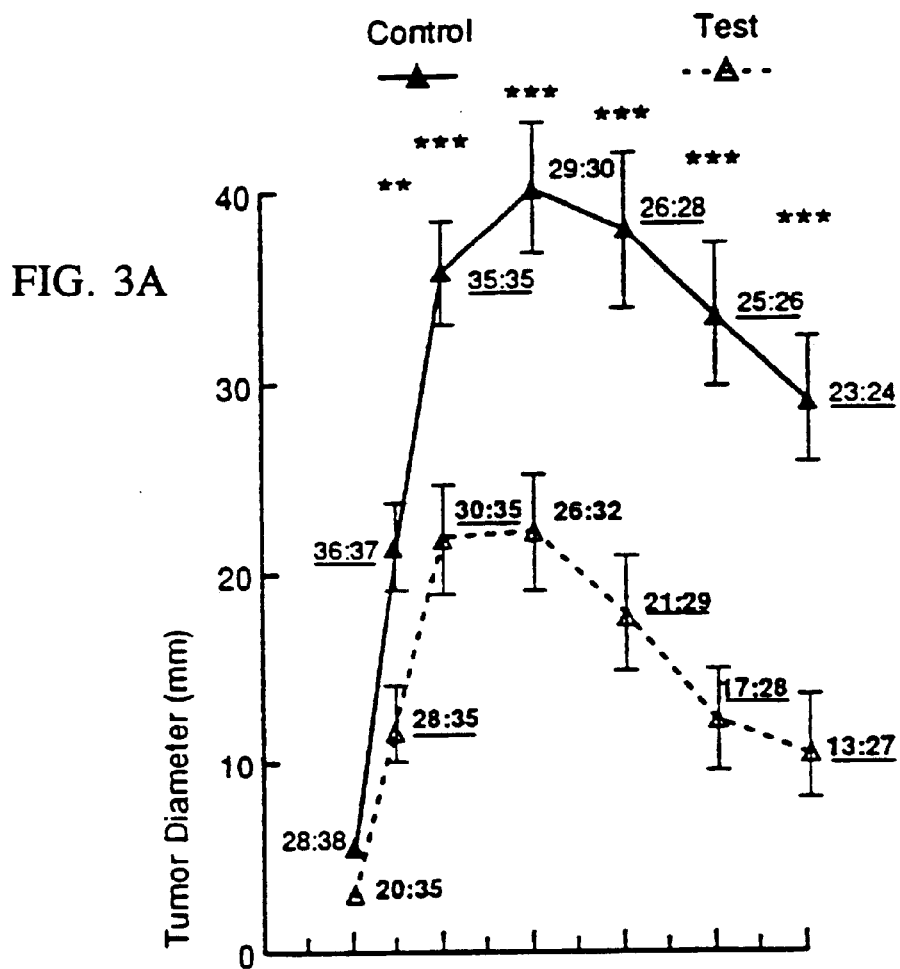
FIGS. 3A and 3B are plots of the growth of challenge (wing web) tumors in TK chickens under conditions of (i) priming with plasmid pVSRC-C1 and heterologous challenge with plasmid pcsrc527 (FIG. 3A: —Δ—, test; —▲—, control) or (ii) priming with pcsrc527 and heterologous challenge with pVSRC-C1 (FIG. 3B: —○—, test; —●—, control). Test chickens were primed at 1 day posthatch with 100 μg of construct; test and control chickens were challenged at five weeks posthatch with 200 μg of construct. The mean challenge tumor diameter was computed as in FIGS. 1A and 1B. At each time point the ratio of chickens bearing palpable challenge tumors to total number of survivors to that point is indicated (standard typeface for control group, bold typeface for test group). Statistical comparisons were made between test and control groups at a particular time point as described for FIGS. 2A and 2B. [*($p<0.05$), ($p<0.01$), *($p<0.001$), for the student's t test], and the paired ratios are underlined for only those time points where, in the chi-squared test, $p<0.05$. Error bars indicate standard error.
Figure 3B:
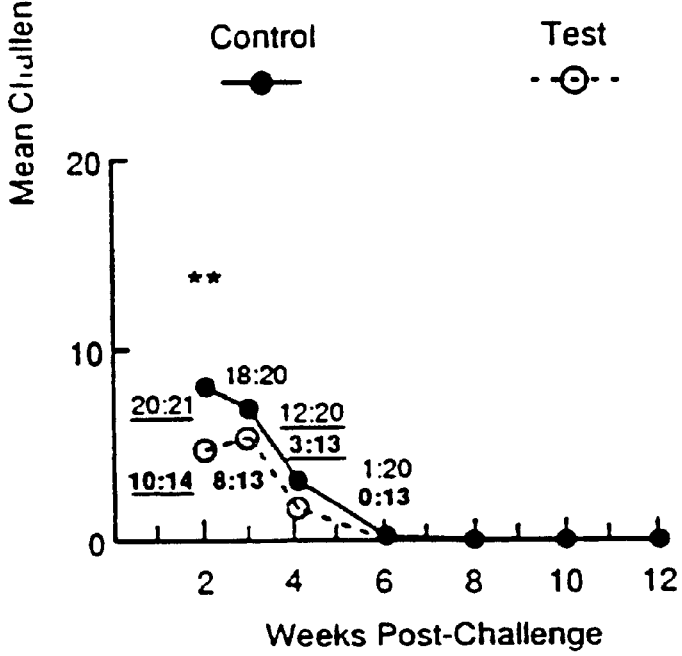

Priming with v-src DNA engenders a relatively greater degree of protection against challenge with c-src(527) DNA, than that afforded by priming with c-src(527) DNA itself (FIG. 3A). The degree of protection was weaker than that determined (FIG. 2B) for the case of priming and homologous challenge with v-src DNA. Only marginal protection was observed, however, when the heterologous challenge protocol was carried out in the reverse order (FIG. 3B). These results demonstrate that induction of reactivity to an antigenicity specified in tumor cells by an overexpressed proto-oncogene can confer tumor immunity.

EXAMPLE 2

Vaccination Protocol

The following is a representative vaccination protocol according to the present invention.

A. Skin Punch Biopsy

A punch biopsy of skin is obtained by a trained physician following standard medical practice.

B. Preparation of Primary Fibroblast Culture

Under sterile conditions, the skin obtained by punch biopsy is put in a tube with 10 ml of the following wash medium: Dulbecco's Modified Eagle Medium (DMEM), containing sodium bicarbonate (30 ml/liter of a 5.6% solution) and penicillin/streptomycin (2 ml/liter of a pen-strep stock solution containing 5000 units penicillin and 5000 µg of streptomycin/ml, pH 7.2–7.4.). In a sterile hood, the skin biopsy is added to a Petri dish, and then transferred several times to new Petri dishes containing the same wash medium. The biopsy is then finely minced with two scalpels, and 2–4 pieces (<1 $mm^3$) of the minced biopsied are placed in the middle part of one or more T25 flasks. The flask is placed in a tissue culture incubator at 37° C. for one half hour with the cap firmly closed, then opened for 10 minutes. The following culture medium is prepared: DMEM containing sodium bicarbonate; antibiotics; and 10% fetal calf serum containing 2.5 µg/ml fungizone, 40 µg/ml gentamicin, and 1% glutamine( 3% W/V). Two ml of the culture medium is then added to the flask, and the flask is incubated at 37° C. (5% $CO_2$), with the cap lightly unscrewed. The flask is left for three days without moving so as to obtain adhesion of the separate pieces of skin to the plastic. Afterwards, the medium is changed two times per week over a 3–4 week period always adding 2–3 ml of medium. To trypsinize the skin cell culture, one needs zones of confluence. After aspirating the culture medium, 5 ml of the Puck's Saline A/EDTA solution (0.4 g EDTA to 1 liter of Puck's Solution A) is added and immediately aspirated. Then 1 ml of trypsin solution (0.05/0.02% trypsin in PBS, without Ca++ or Mg++) is added and incubated for 5 min at 37° C., at which time 2 ml of culture fluid is added to stop the action of the trypsin. The cells are then transferred to a larger flask (T75) and incubated at 37° C. in 15 ml of culture fluid, which is changed every 2 days.

C. Fibroblast Transfection

The fibroblasts ($2 \times 10^5$ cells) are washed twice in DMEM without serum or antibiotics. A LipofectAMINE™-DNA solution is prepared by mixing in tube #1 mix 400 µl DMEM and 10 µl of dCTG vector DNA (1 µg/ul). In tube #2, 400 µl DMEM and 25 Ml of LipofectAMINE Reagent (Life Technologies, cat. no. 18324-012) are mixed. The contents of tube #1 and #2 are mixed together and are then left sitting at room temperature for 30 hours. Then, 3.2 ml of the LipofectAMINE™-DNA solution is added to the cells. The cells are incubated for six hours at 37° C., washed once with Hank's Balanced Salt Solution, and then refed with growth medium and incubated for an additional 24 hours at 37° C.

D. Transfectant Irradiation

Transfectants are irradiated to a dose of 25 By or 2500R. the cells are then counted by trypan blue exclusion. $2 \times 10^7$ irradiated transfectants are resuspended in a volume of 0.2–0.4 ml of Hanks Balanced Salt Solution.

E. Vaccination

Patients are vaccinated by subcutaneous inoculation of $2 \times 10^7$ irradiated cells at 2–3 week intervals. A shorter or longer regimen is used, depending upon the results of delayed type hypersensitivity (DTH) reaction monitoring (described below).

F. Patient Assessment by DTH Monitoring

Patients are assessed for reactivity to the irradiated transfectants by a test of skin reactivity in a DTH reaction, as described by Chang et al. (1993), *Cancer Research* 53:1043–1050. To measure reactivity to the autologous irradiated transfectants, $10^4$–$10^6$ transfected irradiated cells in a volume of 0.1 ml HBSS are inoculated intradermally. Induration is measured 48 hours later, as an average of two perpendicular diameters. Responses of greater than 2 mm are considered positive.

EXAMPLE 3 v-mvc Transfection of Murine Fibroblasts

A. Vector Preparation

The v-myc retroviral oncogene of avian myelocytomatosis virus MC29 (Land et al. (1983), *Nature* 304:596–602) was obtained from the American Type Culture Collection, Rockville, Md., 20852, as the pSVv-myc vector (ATCC No. 45014). The v-myc-positive EcoRI-KpnI fragment of pSVv-myc was ligated into the polylinker sites of the pBK-CMV plasmid (Stratagene Cloning Systems, La Jolla, Cailf.).

B. Cell Transfection

Stable transfection using the pBK-CMV-v-myc vector was carried out on a line of A31 fibroblasts (Balb/c origin), obtained from the ATCC. $2 \times 10^5$ cells were seeded in a 100 mm/dish and allowed to grow for 18–20 h (RPMI 1640 medium and 10% fetal bovine serum), at which time the cells reached 50–70% confluence. The cells were then washed twice in Dulbecco's Modified Eagles Medium (without serum or antibiotics). A LipofectAMINE™-DNA solution was prepared according to Example 2.C., with the pBK-CMV-v-myc vector DNA, and 3.2 ml of the LipofectAMINE™-DNA solution added to the cells. The cells were then incubated for 6 hours at 37° C., washed once with Hank's Balanced Salt Solution, and then refed with the growth medium and incubated for an additional 24 hour at 37° C. Thereafter, the cells were fed once every two days with growth medium containing 250 µg/ml geneticin (G418; Gibco BRL cat. no. 11811) as the selective marker. Within two weeks, colonies were picked and expanded into permanent cell lines. The cells were then washed and collected by centrifugation.

It should be noted that the procedure for transient transfection is the same, through the point of incubation with the Lipofectamine™-DNA solution. Thereafter, the cells are washed and incubated for 72 hours in growth medium.

EXAMPLE 4

Immunization of Mice Against Murine mdm-2-Induced Tumors by Vaccination with Mouse Fibroblasts Transfected with Human mdm-2 Transgene Construct A. Vector An expression vector designated pCMV-Bam-Neo-mdm-2, containing human mdm-2 cDNA, was obtained from Dr. Bert Vogelstein of Johns Hopkins University. The original expression vector pCMV-Bam-Neo, into which the mdm-2 cDNA was inserted, was derived from plasmid BCMGNeo-mIL2 (Karasuyama et al., *J. Exp. Med.* 169, 13, 1989), as described by Baker et al., (1990) *Science* 249:912–915. According to Baker et al., the human beta globin sequences and bovine papilloma virus sequences of plasmid BCMGNeo-mIL2 were excised with Bam HI and Not I. Next, the interleukin-2 sequences present at the unique Xho I site were removed, and the Xho I site was changed to a Bam HI site by linker addition. The vector includes CMV promoter/enhancer sequences for driving expression of the insert at the Bam HI site. The vector also includes splicing and polyadenylation sites derived from the rabbit beta globin gene, which ensure proper processing of the transcribed insert in the cells. A pBR322 origin of replication and beta-lactamase gene facilitate growth of the plasmid in *Escherichia coli*. The plasmid conferred geneticin resistance through expression of the neomycin resistance gene under separate control of an HSV thymidine kinase promoter. The neomycin resistance gene allows for selection of transfected cells in geneticin.

B. Fibroblast Preparation

A31 fibroblasts available from ATCC were seeded in 150 mM tissue culture dishes ($5 \times 10^5$ cells per dish) at 37° C. and grown in DMEM containing 10% fetal bovine serum and penicillin/streptomycin until the cells reached 80% confluence.

C. Fibroblast Transfection

The expression vector pCMV-Bam-Neo-mdm-2 was used as follows to introduce human mdm-2 cDNA into fibroblast cells. pCMV-Bam-Neo was used as a control vector.

Fifteen samples (in fifteen separate 15 ml polypropylene tubes) of each of the following mixtures were prepared: Mixture #1: 2.4 ml DMEM (no serum or antibiotics), plus 15 µg of pCMV-Bam-Neo DNA; Mixture #2: 2.4 ml DMEM (no serum or antibiotics), plus 15 µg of pCMV-Bam-Neo-mdm-2 DNA. Thirty samples (in thirty separate 15 ml polypropylene tubes) of a Mixture #3 were prepared: 2.4 ml DMEM (no serum or antibiotics), plus 75 µl LipofectAMINE Reagent (Gibco BRL, Gaithersburg, Md.). The contents of the fifteen tubes containing Mixture #1 were combined with the contents of fifteen of the Mixture #3 tubes. Similarly, the contents of the fifteen Mixture #2 tubes were combined with the remaining fifteen Mixture #3 tubes. The result was two sets of samples:

Set A: DMEM/pCMV-Bam-Neo+DMEM/LipofectAMINE (15 tubes);

Set B: DMEM/pCMV-Bam-Neo-mdm-2+DMEM/LipofectAMINE (15 tubes).

The A31 cells in the thirty 150 mM tissue culture dishes were washed with 10 ml DMEM (no serum or antibiotics). Then 11.2 ml DMEM (no serum or antibiotics) was added to each dish. After 30 minutes incubation, 10 ml DMEM (no serum or antibiotics) was added to each of the thirty sample tubes with mixing, and the sample tube contents were placed directly onto the A31 cells in the thirty 150 mM tissue culture dishes. The cells were incubated at 37° C. for seven more hours, washed with 10 ml Hanks Balanced Salt Solution and refed with DMEM containing 10% fetal bovine serum (no antibiotics). The cells were incubated at 37° C. for seven hours and then washed with 10 ml Hanks Balanced Salt Solution. Then, 4 ml of trypsin was added to the cells, and the cells were incubated at 37° C. until they became detached from the tissue culture dishes. Six ml of DMEM containing 10% fetal bovine serum (no antibiotics) was then added to each culture dish. The cells from each set were pooled and placed into three 50 ml polypropylene tubes and centrifuged at 500×g to pellet the cells. The media was removed and the cell pellets were resuspended in 4 ml freezing media (90% iron enriched calf serum/10% DMSO). The cells were allowed to sit overnight at −80° C., and then were transferred to a liquid nitrogen storage tank.

D. Vaccination and Challenge

Balb/c-H-$2^k$ mice, which are histocompatible with the A31 cellular inmmunogen and SP2 challenge tumor cells (SP2 plasmacytoma cells, available from ATCC), were used as hosts for vaccination and challenge. Animals received PBS (Group 1, control); A31 cells transfected the pCMV-Bam-Neo control expression construct in PBS (Group 2); or A31 cells transfected the pCMV-Bam-Neo-mdm-2 expression construct in PBS (Group 3). The cells for injection were washed twice with cold, sterile phosphate-buffered saline supplemented with penicillin/streptomycin. Each animal received three vaccinations, two weeks apart, via intraperitoneal injection. $5 \times 10^5$ cells in 100 µl of PBS was used for each injection. Each injected group of animal contained ten individuals. Following the six-week vaccination period, the animals were challenged by subcutaneous injection with $5 \times 10^5$ syngeneic mouse plasmacytoma SP2 cells. The SP2 cells overexpresses the mdm-2 proto-oncogene (Berberich et al., (1994) *Oncogene* 9(5):1469–72). Subcutaneous tumor growth in all animals was evaluated and compared with control animals. The results appear in FIG. 4.

Figure 4:
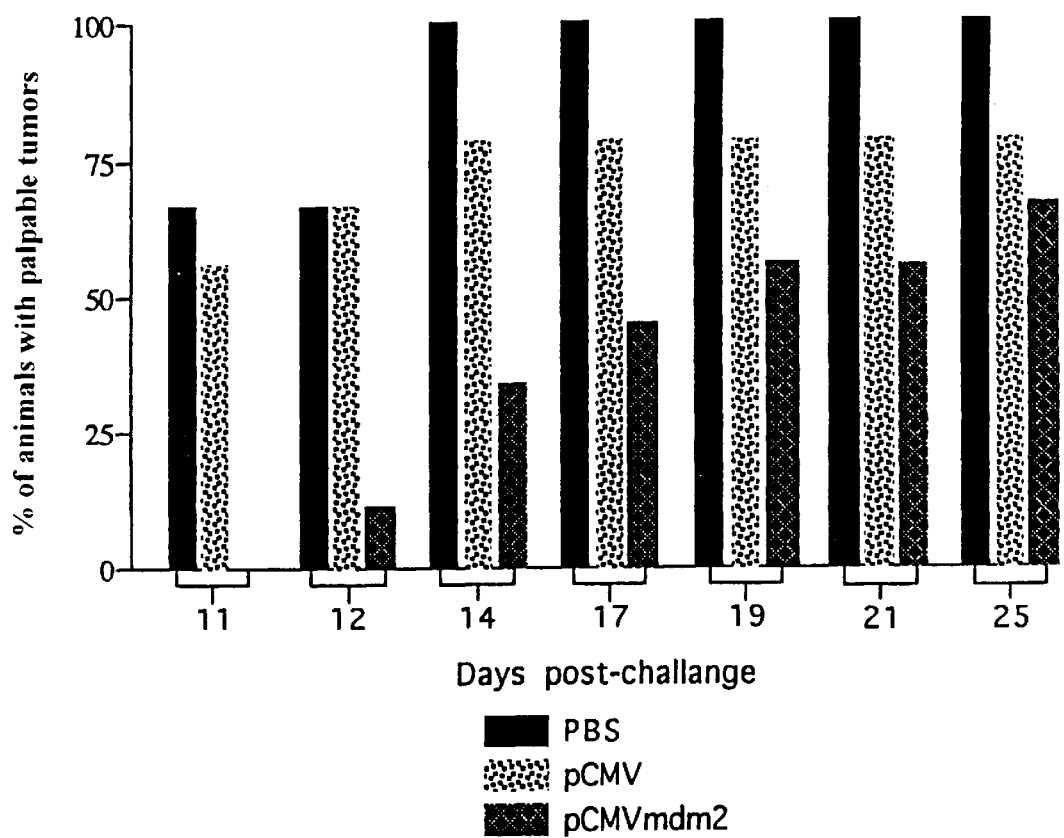
FIG. 4 is a graph of the growth of transplanted, subcutaneous SP2 plasmacytomas in Balb/c mice following inoculation with phosphate-buffered saline (PBS), or priming with syngeneic fibroblasts transfected with either expression vector containing human mdm-2 DNA (pCMVmdm2) or with control expression vector (pCMV). Following inoculation, animals were challenged by subcutaneous injection with $5\times10^5$ syngeneic mouse plasmacytoma SP2 cells which overexpresses the mdm-2 proto-oncogene. The percentage of animals with palpable tumors was determined on days 11, 12, 14, 17, 19, 21 and 25 post challenge.

A comparison of the time of appearance of palpable tumors induced by the subcutaneous transplantation of SP2 tumor cells into mice showed that there was a substantial delay in the appearance of tumors in mice which had been previously inoculated with syngeneic fibroblasts transfected with DNA encoding human mdm-2 protein (pCMV-Bam-Neo-mdm-2) (FIG. 4, pCMVmdm2) as compared to mice which had been inoculated either with vector DNA lacking human mdm-2 (pCMB-Bam-Neo) (FIG. 4, pCMV) or with PBS (FIG. 4, PBS). These results demonstrate that prior inoculation with a cell-based immunogen expressing the cognate human mdm-2 proto-oncogene elicits tumor immunity that causes a delay in the appearance of palpable tumors in which there is overexpression of the cognate murine proto-oncogene. These data indicate that the vaccination principle, i.e., syngeneic fibroblasts transfected with a cognate oncogene, serves to induce tumor immunity in an experimental model of mammalian tumor growth.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A cellular immunogen for use in a mammalian host comprising host cells which have been transfected with at least one vector comprising at least one cognate proto-oncogene deleted in a region which encodes an amino acid sequence required for transformation and which consists of wildtype sequences outside the deletion site and a strong promoter to drive the expression of the cognate proto-oncogene in the transfected cells, wherein said cognate proto-oncogene is non-transforming, and wherein the host cells are selected from the group consisting of professional antigen-presenting cells, fibroblasts and cells obtained from a skin punch biopsy.

2. An immunogen according to claim 1 wherein the transfected cells are non-dividing.

3. An immunogen according to claim 1 wherein the host cells have been transfected with a cognate proto-oncogene selected from the group consisting of AKT-2, c-erbB-2, mdm-2, c-myc, c-myb, c-ras, c-src and c-yes.

4. An immunogen according to claim 1 wherein the cells comprise fibroblasts.

5. A method for preparing a cellular immunogen for use in a mammalian host comprising:
   (a) excising cells from the host;
   (b) transfecting the excised cells with at least one vector comprising at least one cognate proto-oncogene deleted in a region which encodes an amino acid sequence required for transformation and which consists of wild-type sequences outside the deletion site and a promoter to drive the expression of the cognate proto-oncogene in the transfected cells,
wherein said cognate proto-oncogene is non-transforming and is cognate to a target proto-oncogene, and wherein the cells are selected from the group consisting of professional antigen-presenting cells, fibroblasts and cells obtained from a skin punch biopsy.

6. A method according to claim 5 wherein the transfected cells are non-dividing.

7. A method according to claim 5 wherein the cognate proto-oncogene is selected from the group consisting of AKT-2, c-erbB2, mdm-2, c-myc, c-myb, c-ras, c-src and c-yes.

8. A method according to claim 5 wherein the excised cells comprise fibroblasts.

9. A method of delaying onset of tumor growth in a mammalian host at risk for developing a tumor, which tumor is characterized by the overexpression of a target proto-oncogene, comprising:
   (a) excising cells from the host;
   (b) transfecting the excised cells with at least one vector comprising at least one cognate proto-oncogene and a promoter to drive the expression of the cognate proto-oncogene in the transfected cells; and
   (c) returning the excised cells transfected with the vector to the body of the host to obtain expression of the cognate proto-oncogene in the host,
wherein the transfected cells are selected from the group consisting of professional antigen-presenting cells, fibroblasts and cells obtained from a skin punch biopsy, and wherein the cognate proto-oncogene is cognate to the target proto-oncogene and encodes a gene product which induces host immunoreactivity to host self-determinants of the product of the target proto-oncogene.

10. A method according to claim 9 wherein the transfected cells are rendered non-dividing prior to return to the body of the host.

11. A method according to claim 9 wherein the cognate proto-oncogene is selected from the group consisting of AKT-2, c-erbB2, mdm-2, c-myc, c-myb, c-ras, c-src and c-yes.

12. A method according to claim 9 wherein the excised host cells comprise fibroblasts.

13. An immunogen according to claim 1 wherein the professional antigen-presenting cells are selected from the group consisting of macrophages and dendritic cells.

14. A method according to claim 5 wherein the professional antigen-presenting cells are selected from the group consisting of macrophages and dendritic cells.

15. A method according to claim 9 wherein the professional antigen-presenting cells are selected from the group consisting of macrophages and dendritic cells.

16. A method according to claim 9 wherein the transfected cells are returned to the body of the host by subcutaneous, intradermal or intraperitoneal administration.

17. A method of generating an immune response in a mammalian host at risk for developing a tumor, wherein the tumor is characterized by the overexpression of a target proto-oncogene, comprising:
   (a) excising cells from the host, wherein the cells are selected from the group consisting of professional antigen-presenting cells, fibroblasts and cells obtained from a skin punch biopsy;
   (b) transfecting the excised cells with at least one vector comprising at least one cognate proto-oncogene and a promoter to drive the expression of the cognate proto-oncogene in the transfected cells, wherein the cognate proto-oncogene is cognate to the target proto-oncogene and encodes a gene product which induces host immunoreactivity to host self-determinants of the product of the target proto-oncogene; and
   (c) returning the excised cells transfected with the vector to the body of the host to obtain expression of the cognate proto-oncogene in the host,
wherein the immune response delays onset of tumor growth.

18. A method according to claim 13 wherein the transfected cells are rendered non-dividing prior to return to the body of the host.

19. A method according to claim 17 wherein the transfected cells are returned to the body of the host by subcutaneous, intradermal or intraperitoneal administration.

20. A method according to claim 17 wherein the cognate proto-oncogene is selected from the group consisting of AKT-2, c-erbB-2, mdm-2, c-myc, c-myb, c-ras, c-src and c-yes.

21. A method according to claim 17 wherein the excised host cells comprise fibroblasts.

22. A method according to claim 17 wherein the professional antigen-presenting cells are selected from the group consisting of macrophages and dendritic cells.

* * * * *

UNITED STATES PATENT AND TRADEMARK OFFICE
CERTIFICATE OF CORRECTION

PATENT NO. : 6,365,151 B1
DATED : April 2, 2002
INVENTOR(S) : Michael S. Halpern and James M. England It is certified that error appears in the above-identified patent and that said Letters Patent is hereby corrected as shown below:

<u>Title page,</u>
Item [54], "PROTO-OXOGENES" to -- PROTO-ONCOGENES --

Signed and Sealed this

Fourteenth Day of January, 2003

JAMES E. ROGAN
*Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 1:

CCAGTTCCAG CCTGGAGAGA ACCTATA                                      27

(2) INFORMATION FOR SEQ ID NO: 2:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 2:

GATCTATAGG TTCTCTCCAG GCTGGAACTG GGGCT                                      35

(2) INFORMATION FOR SEQ ID NO: 3:

(i) SEQUENCE CHARACTERISTICS:
        (A) LENGTH: 1599 base pairs
        (B) TYPE: nucleic acid
        (C) STRANDEDNESS: single
        (D) TOPOLOGY: linear (xi) SEQUENCE DESCRIPTION: SEQ ID NO: 3:

GAGACTGTGC CCTGTCCACG GTGCCTCCTG CATGTCCTGC TGCCCTGAGC T GTCCCGAGC           60
TAGGTGACAG CGTACCACGC TGCCACCATG AATGAGGTGT CTGTCATCAA A GAAGGCTGG         120
CTCCACAAGC GTGGTGAATA CATCAAGACC TGGAGGCCAC GGTACTTCCT G CTGAAGAGC         180
GACGGCTCCT TCATTGGGTA CAAGGAGAGG CCCGAGGCCC TGATCAGAC T CTACCCCCC          240
TTAAACAACT TCTCCGTAGC AGAATGCCAG CTGATGAAGA CCGAGAGGCC G CGACCCAAC         300
ACCTTTGTCA TACGCTGCCT GCAGTGGACC ACAGTCATCG AGGACCTT C CACGTGGAT           360
TCTCCAGACG AGAGGGAGGA GTGGATGCGG GCCATCCAGA TGGTCGCCAA C AGCCTCAAG         420
CAGCGGGCCC CAGGCGAGGA CCCCATGGAC TACAAGTGTG CTCCCCCAG T GACTCCTCC          480
ACGACTGAGG AGATGGAAGT GGCGGTCAGC AAGGCACGGG CTAAAGTGAC C ATGAATGAC         540
TTCGACTATC TCAAACTCCT TGGCAAGGGA ACCTTTGGCA AAGTCATCCT G GTGCGGGAG         600
AAGGCCACTG GCCGCTACTA CGCCATGAAG ATCCTGCGAA AGGAAGTCAT C ATTGCCAAG         660
GATGAAGTCG CTCACACAGT CACCGAGAGC CGGGTCCTCC AGAACACCAG G CACCCGTTC         720
CTCACTGCGC TGAAGTATGC CTTCCAGACC CACGACCGCC TGTGCTTTGT G ATGGAGTAT         780
GCCAACGGGG GTGAGCTGTT CTTCCACCTG TCCCGGGAGC GTGTCTTCAC A GAGGAGCGG         840
GCCCGGTTTT ATGGTGCAGA GATTGTCTCG GCTCTTGAGT ACTTGCACTC G CGGGACGTG         900
GTATACCGCG ACATCAAGCT GGAAAACCTC ATGCTGGACA AGATGGCCA C ATCAAGATC          960
ACTGACTTTG GCCTCTGCAA AGAGGGCATC AGTGACGGGG CCACCATGAA A ACCTTCTGT        1020
GGGACCCCGG AGTACCTGGC GCCTGAGGTG CTGGAGGACA ATGACTATGG C CGGGCCGTG        1080
GACTGGTGGG GGCTGGGTGT GGTCATGTAC GAGATGATGT GCGGCCGCCT G CCCTTCTAC        1140
AACCAGGACC ACGAGCGCCT CTTCGAGCTC ATCCTCATGG AAGAGATCCG C TTCCCGCGC        1200
ACGCTCAGCC CCGAGGCCAA GTCCCTGCTT GCTGGGCTGC TTAAGAAGGA C CCCAAGCAG        1260
AGGCTTGGTG GGGGGCCCAG CGATGCCAAG GAGGTCATGG AGCACAGGTT C TTCCTCAGC        1320
ATCAACTGGC AGGACGTGGT CCAGAAGAAG CTCCTGCCAC CCTTCAAACC T CAGGTCACG        1380
TCCGAGGTCG ACACAAGGTA CTTCGATGAT GAATTTACCG CCCAGTCCAT C ACAATCACA        1440
CCCCCTGACC GCTATGACAG CCTGGGCTTA CTGGAGCTGG ACCAGCGGAC C CACTTCCCC        1500
CAGTTCTCCT ACTCGGCCAG CATCCGCGAG TGAGCAGTCT GCCCACGCAG A GGACGCACG        1560
CTCGCTGCCA TCACCGCTGG GTGGTTTTTT ACCCCTGCC                               1599

(2) INFORMATION FOR SEQ ID NO: 4:

(i) SEQUENCE CHARACTERISTICS:
        (A) LENGTH: 4530 base pairs
        (B) TYPE: nucleic acid
        (C) STRANDEDNESS: single
        (D) TOPOLOGY: linear (xi) SEQUENCE DESCRIPTION: SEQ ID NO: 4:

-continued

```
AATTCTCGAG CTCGTCGACC GGTCGACGAG CTCGAGGGTC GACGAGCTCG A GGGCGCGCG      60

CCCGGCCCCC ACCCCTCGCA GCACCCCGCG CCCCGCGCCC TCCCAGCCGG G TCCAGCCGG     120

AGCCATGGGG CCGGAGCCGC AGTGAGCACC ATGGAGCTGG CGGCCTTGTG C CGCTGGGGG    180

CTCCTCCTCG CCCTCTTGCC CCCCGGAGCC GCGAGCACCC AAGTGTGCAC C GGCACAGAC    240

ATGAAGCTGC GGCTCCCTGC CAGTCCCGAG ACCCACCTGG ACATGCTCCG C CACCTCTAC    300

CAGGGCTGCC AGGTGGTGCA GGGAAACCTG GAACTCACCT ACCTGCCCAC C AATGCCAGC    360

CTGTCCTTCC TGCAGGATAT CCAGGAGGTG CAGGGCTACG TGCTCATCGC T CACAACCAA    420

GTGAGGCAGG TCCCACTGCA GAGGCTGCGG ATTGTGCGAG GCACCCAGCT C TTTGAGGAC    480

AACTATGCCC TGGCCGTGCT AGACAATGGA GACCCGCTGA ACAATACCAC C CCTGTCACA    540

GGGGCCTCCC CAGGAGGCCT GCGGGAGCTG CAGCTTCGAA GCCTCACAGA G ATCTTGAAA    600

GGAGGGGTCT TGATCCAGCG GAACCCCCAG CTCTGCTACC AGGACACGAT T TTGTGGAAG    660

GACATCTTCC ACAAGAACAA CCAGCTGGCT CTCACACTGA TAGACACCAA C CGCTCTCGG    720

GCCTGCCACC CCTGTTCTCC GATGTGTAAG GGCTCCCGCT GCTGGGGAGA G AGTTCTGAG    780

GATTGTCAGA GCCTGACGCG CACTGTCTGT GCCGGTGGCT GTGCCCGCTG C AAGGGGCCA    840

CTGCCCACTG ACTGCTGCCA TGAGCAGTGT GCTGCCGGCT GCACGGGCCC C AAGCACTCT    900

GACTGCCTGG CCTGCCTCCA CTTCAACCAC AGTGGCATCT GTGAGCTGCA C TGCCCAGCC    960

CTGGTCACCT ACAACACAGA CACGTTTGAG TCCATGCCCA ATCCCGAGGG C CGGTATACA   1020

TTCGGCGCCA GCTGTGTGAC TGCCTGTCCC TACAACTACC TTTCTACGGA C GTGGGATCC   1080

TGCACCCTCG TCTGCCCCCT GCACAACCAA GAGGTGACAG CAGAGGATGG A ACACAGCGG   1140

TGTGAGAAGT GCAGCAAGCC CTGTGCCCGA GTGTGCTATG GTCTGGGCAT G GAGCACTTG   1200

CGAGAGGTGA GGGCAGTTAC CAGTGCCAAT ATCCAGGAGT TTGCTGGCTG C AAGAAGATC   1260

TTTGGGAGCC TGGCATTTCT GCCGGAGAGC TTTGATGGGG ACCCAGCCTC C AACACTGCC   1320

CCGCTCCAGC CAGAGCAGCT CCAAGTGTTT GAGACTCTGG AAGAGATCAC A GGTTACCTA   1380

TACATCTCAG CATGGCCGGA CAGCCTGCCT GACCTCAGCG TCTTCCAGAA C CTGCAAGTA   1440

ATCCGGGGAC GAATTCTGCA CAATGGCGCC TACTCGCTGA CCCTGCAAGG G CTGGGCATC   1500

AGCTGGCTGG GGCTGCGCTC ACTGAGGGAA CTGGGCAGTG GACTGGCCCT C ATCCACCAT   1560

AACACCCACC TCTGCTTCGT GCACACGGTG CCCTGGGACC AGCTCTTTCG G AACCCGCAC   1620

CAAGCTCTGC TCCACACTGC CAACCGGCCA GAGGACGAGT GTGTGGGCGA G GGCCTGGCC   1680

TGCCACCAGC TGTGCGCCCG AGGGCACTGC TGGGGTCCAG GCCCACCCA G TGTGTCAAC   1740

TGCAGCCAGT TCCTTCGGGG CCAGGAGTGC GTGGAGGAAT GCCGAGTACT G CAGGGGCTC   1800

CCCAGGGAGT ATGTGAATGC CAGGCACTGT TTGCCGTGCC ACCCTGAGTG T CAGCCCCAG   1860

AATGGCTCAG TGACCTGTTT TGGACCGGAG GCTGACCAGT GTGTGGCCTG T GCCCACTAT   1920

AAGGACCCTC CCTTCTGCGT GGCCCGCTGC CCCAGCGGTG TGAAACCTGA C CTCTCCTAC   1980

ATGCCCATCT GGAAGTTTCC AGATGAGGAG GGCGCATGCC AGCCTTGCCC C ATCAACTGC   2040

ACCCACTCCT GTGTGGACCT GGATGACAAG GGCTGCCCCG CCGAGCAGAG A GCCAGCCCT   2100

CTGACGTCCA TCGTCTCTGC GGTGGTTGGC ATTCTGCTGG TCGTGGTCTT G GGGGTGGTC   2160

TTTGGGATCC TCATCAAGCG ACGGCAGCAG AAGATCCGGA AGTACACGAT G CGGAGACTG   2220

CTGCAGGAAA CGGAGCTGGT GGAGCCGCTG ACACCTAGCG GAGCGATGCC C AACCAGGCG   2280

CAGATGCGGA TCCTGAAAGA GACGGAGCTG AGGAAGGTGA AGGTGCTTGG A TCTGGCGCT   2340

TTTGGCACAG TCTACAAGGG CATCTGGATC CCTGATGGGG AGAATGTGAA A ATTCCAGTG   2400
```

-continued

```
GCCATCAAAG TGTTGAGGGA AAACACATCC CCCAAAGCCA ACAAAGAAAT C TTAGACGAA    2460

GCATACGTGA TGGCTGGTGT GGGCTCCCCA TATGTCTCCC GCCTTCTGGG C ATCTGCCTG    2520

ACATCCACGG TGCAGCTGGT GACACAGCTT ATGCCCTATG GCTGCCTCTT A GACCATGTC    2580

CGGGAAAACC GCGGACGCCT GGGCTCCCAG GACCTGCTGA ACTGGTGTAT G CAGATTGCC    2640

AAGGGGATGA GCTACCTGGA GGATGTGCGG CTCGTACACA GGGACTTGGC C GCTCGGAAC    2700

GTGCTGGTCA AGAGTCCCAA CCATGTCAAA ATTACAGACT TCGGGCTGGC T CGGCTGCTG    2760

GACATTGACG AGACAGAGTA CCATGCAGAT GGGGGCAAGG TGCCCATCAA G TGGATGGCG    2820

CTGGAGTCCA TTCTCCGCCG GCGGTTCACC CACCAGAGTG ATGTGTGGAG T TATGGTGTG    2880

ACTGTGTGGG AGCTGATGAC TTTTGGGGCC AAACCTTACG ATGGGATCCC A GCCCGGGAG    2940

ATCCCTGACC TGCTGGAAAA GGGGGAGCGG CTGCCCCAGC CCCCCATCTG C ACCATTGAT    3000

GTCTACATGA TCATGGTCAA ATGTTGGATG ATTGACTCTG AATGTCGGCC A AGATTCCGG    3060

GAGTTGGTGT CTGAATTCTC CCGCATGGCC AGGGACCCCC AGCGCTTTGT G GTCATCCAG    3120

AATGAGGACT TGGGCCCAGC CAGTCCCTTG GACAGCACCT TCTACCGCTC A CTGCTGGAG    3180

GACGATGACA TGGGGGACCT GGTGGATGCT GAGGAGTATC TGGTACCCCA G CAGGGCTTC    3240

TTCTGTCCAG ACCCTGCCCC GGGCGCTGGG GGCATGGTCC ACCACAGGCA C CGCAGCTCA    3300

TCTACCAGGA GTGGCGGTGG GGACCTGACA CTAGGGCTGG AGCCCTCTGA A GAGGAGGCC    3360

CCCAGGTCTC CACTGGCACC CTCCGAAGGG GCTGGCTCCG ATGTATTTGA T GGTGACCTG    3420

GGAATGGGGG CAGCCAAGGG GCTGCAAAGC CTCCCCACAC ATGACCCCAG C CCTCTACAG    3480

CGGTACAGTG AGGACCCCAC AGTACCCCTG CCCTCTGAGA CTGATGGCTA C GTTGCCCCC    3540

CTGACCTGCA GCCCCAGCC TGAATATGTG AACCAGCCAG ATGTTCGGCC C CAGCCCCCT    3600

TCGCCCCGAG AGGGCCCTCT GCCTGCTGCC CGACCTGCTG GTGCCACTCT G GAAAGGGCC    3660

AAGACTCTCT CCCCAGGGAA GAATGGGGTC GTCAAAGACG TTTTTGCCTT T GGGGGTGCC    3720

GTGGAGAACC CCGAGTACTT GACACCCCAG GGAGGAGCTG CCCCTCAGCC C CACCCTCCT    3780

CCTGCCTTCA GCCCAGCCTT CGACAACCTC TATTACTGGG ACCAGGACCC A CCAGAGCGG    3840

GGGGCTCCAC CCAGCACCTT CAAAGGGACA CCTACGGCAG AGAACCCAGA G TACCTGGGT    3900

CTGGACGTGC CAGTGTGAAC CAGAAGGCCA AGTCCGCAGA AGCCCTGATG T GTCCTCAGG    3960

GAGCAGGGAA GGCCTGACTT CTGCTGGCAT CAAGAGGTGG GAGGGCCCTC C GACCACTTC    4020

CAGGGGAACC TGCCATGCCA GGAACCTGTC CTAAGGAACC TTCCTTCCTG C TTGAGTTCC    4080

CAGATGGCTG GAAGGGGTCC AGCCTCGTTG GAAGAGGAAC AGCACTGGGG A GTCTTTGTG    4140

GATTCTGAGG CCCTGCCCAA TGAGACTCTA GGGTCCAGTG GATGCCACAG C CCAGCTTGG    4200

CCCTTTCCTT CCAGATCCTG GGTACTGAAA GCCTTAGGGA AGCTGGCCTG A GAGGGGAAG    4260

CGGCCCTAAG GGAGTGTCTA AGAACAAAAG CGACCCATTC AGAGACTGTC C CTGAAACCT    4320

AGTACTGCCC CCCATGAGGA AGGAACAGCA ATGGTGTCAG TATCCAGGCT T TGTACAGAG    4380

TGCTTTTCTG TTTAGTTTTT ACTTTTTTTG TTTTGTTTTT TTAAAGACGA A ATAAAGACC    4440

CAGGGGAGAA TGGGTGTTGT ATGGGGAGGC AAGTGTGGGG GGTCCTTCTC C ACACCCACT    4500

TTGTCCATTT GCAAATATAT TTTGGAAAAC                                     4530
```

(2) INFORMATION FOR SEQ ID NO: 5:

(i) SEQUENCE CHARACTERISTICS:
        (A) LENGTH: 891 base pairs
        (B) TYPE: nucleic acid (C) STRANDEDNESS: single
          (D) TOPOLOGY: linear (xi) SEQUENCE DESCRIPTION: SEQ ID NO: 5:

ATGTGCAATA CCAACATGTC TGTACCTACT GATGGTGCTG TAACCACCTC A CAGATTCCA      60

GCTTCGGAAC AAGAGACCCT GGATCTTGAT GCTGGTGTAA GTGAACATTC A GGTGATTGG     120

TTGGATCAGG ATTCAGTTTC AGATCAGTTT AGTGTAGAAT TTGAAGTTGA A TCTCTCGAC    180

TCAGAAGATT ATAGCCTTAG TGAAGAAGGA CAAGAACTCT CAGATGAAGA T GATGAGGTA    240

TATCAAGTTA CTGTGTATCA GGCAGGGGAG AGTGATACAG ATTCATTTGA A GAAGATCCT    300

GAAATTTCCT TAGCTGACTA TTGGAAATGC ACTTCATGCA ATGAAATGAA T CCCCCCCTT    360

CCATCACATT GCAACAGATG TTGGGCCCTT CGTGAGAATT GGCTTCCTGA A GATAAAGGG    420

AAAGATAAAG GGGAAATCTC TGAGAAAGCC AAACTGGAAA ACTCAACACA A GCTGAAGAG    480

GGCTTTGATG TTCCTGATTG TAAAAAAACT ATAGTGAATG ATTCCAGAGA G TCATGTGTT    540

GAGGAAAATG ATGATAAAAT TACACAAGCT TCACAATCAC AAGAAAGTGA A GACTATTCT    600

CAGCCATCAA CTTCTAGTAG CATTATTTAT AGCAGCCAAG AAGATGTGAA A GAGTTTGAA    660

AGGGAAGAAA CCCAAGACAA AGAAGAGAGT GTGGAATCTA GTTTGCCCCT T AATGCCATT    720

GAACCTTGTG TGATTTGTCA AGGTCGACCT AAAAATGGTT GCATTGTCCA T GGCAAAACA    780

GGACATCTTA TGGCCTGCTT TACATGTGCA AAGAAGCTAA AGAAAAGGAA T AAGCCCTGC    840

CCAGTATGTA GACAACCAAT TCAAATGATT GTGCTAACTT ATTTCCCCTA G             891

(2) INFORMATION FOR SEQ ID NO: 6:

(i) SEQUENCE CHARACTERISTICS:
         (A) LENGTH: 657 base pairs
         (B) TYPE: nucleic acid
         (C) STRANDEDNESS: single
         (D) TOPOLOGY: linear (xi) SEQUENCE DESCRIPTION: SEQ ID NO: 6:

ATGTGCAATA CCAACATGTC TGTACCTACT GATGGTGCTG TAACCACCTC A CAGATTCCA      60

GCTTCGGAAC AAGAGACCCT GGACTATTGG AAATGCACTT CATGCAATGA A ATGAATCCC    120

CCCCTTCCAT CACATTGCAA CAGATGTTGG GCCCTTCGTG AGAATTGGCT T CCTGAAGAT    180

AAAGGGAAAG ATAAAGGGGA AATCTCTGAG AAAGCCAAAC TGGAAAACTC A ACACAAGCT    240

GAAGAGGGCT TTGATGTTCC TGATTGTAAA AAAACTATAG TGAATGATTC C AGAGAGTCA    300

TGTGTTGAGG AAAATGATGA TAAAATTACA CAAGCTTCAC AATCACAAGA A AGTGAAGAC    360

TATTCTCAGC CATCAACTTC TAGTAGCATT ATTTATAGCA GCCAAGAAGA T GTGAAAGAG    420

TTTGAAAGGG AAGAAACCCA AGACAAAGAA GAGAGTGTGG AATCTAGTTT G CCCCTTAAT    480

GCCATTGAAC CTTGTGTGAT TTGTCAAGGT CGACCTAAAA ATGGTTGCAT T GTCCATGGC    540

AAAACAGGAC ATCTTATGGC CTGCTTTACA TGTGCAAAGA AGCTAAAGAA A AGGAATAAG    600

CCCTGCCCAG TATGTAGACA ACCAATTCAA ATGATTGTGC TAACTTATTT C CCCTAG       657

(2) INFORMATION FOR SEQ ID NO: 7:

(i) SEQUENCE CHARACTERISTICS:
         (A) LENGTH: 966 base pairs
         (B) TYPE: nucleic acid
         (C) STRANDEDNESS: single
         (D) TOPOLOGY: linear (xi) SEQUENCE DESCRIPTION: SEQ ID NO: 7:

-continued

```
ATGTGCAATA CCAACATGTC TGTACCTACT GATGGTGCTG TAACCACCTC A CAGATTCCA      60

GCTTCGGAAC AAGAGACCCT GGTTAGACCA AAGCCATTGC TTTTGAAGTT A TTAAAGTCT     120

GTTGGTGCAC AAAAAGACAC TTATACTATG AAAGAGGATC TTGATGCTGG T GTAAGTGAA     180

CATTCAGGTG ATTGGTTGGA TCAGGATTCA GTTTCAGATC AGTTTAGTGT A GAATTTGAA     240

GTTGAATCTC TCGACTCAGA AGATTATAGC CTTAGTGAAG AAGGACAAGA A CTCTCAGAT     300

GAAGATGATG AGGTATATCA AGTTACTGTG TATCAGGCAG GGGAGAGTGA T ACAGATTCA     360

TTTGAAGAAG ATCCTGAAAT TTCCTTAGCT GACTATTGGA AATGCACTTC A TGCAATGAA     420

ATGAATCCCC CCCTTCCATC ACATTGCAAC AGATGTTGGG CCCTTCGTGA G AATTGGCTT     480

CCTGAAGATA AAGGGAAAGA TAAAGGGGAA ATCTCTGAGA AAGCCAAACT G GAAAACTCA     540

ACACAAGCTG AAGAGGGCTT TGATGTTCCT GATTGTAAAA AAACTATAGT G AATGATTCC     600

AGAGAGTCAT GTGTTGAGGA AAATGATGAT AAAATTACAC AAGCTTCACA A TCACAAGAA     660

AGTGAAGACT ATTCTCAGCC ATCAACTTCT AGTAGCATTA TTTATAGCAG C CAAGAAGAT     720

GTGAAAGAGT TTGAAAGGGA AGAAACCCAA GACAAAGAAG AGAGTGTGGA A TCTAGTTTG     780

CCCCTTAATG CCATTGAACC TTGTGTGATT TGTCAAGGTC GACCTAAAAA T GGTTGCATT     840

GTCCATGGCA AAACAGGACA TCTTATGGCC TGCTTTACAT GTGCAAAGAA G CTAAAGAAA     900

AGGAATAAGC CCTGCCCAGT ATGTAGACAA CCAATTCAAA TGATTGTGCT A ACTTATTTC     960

CCCTAG                                                                 966

(2) INFORMATION FOR SEQ ID NO: 8:

(i) SEQUENCE CHARACTERISTICS:
        (A) LENGTH: 399 base pairs
        (B) TYPE: nucleic acid
        (C) STRANDEDNESS: single
        (D) TOPOLOGY: linear (xi) SEQUENCE DESCRIPTION: SEQ ID NO: 8:

ATGTGCAATA CCAACATGTC TGTACCTACT GATGGTGCTG TAACCACCTC A CAGATTCCA      60

GCTTCGGAAC AAGAGACCCT GGTTAGACAA GAAAGTGAAG ACTATTCTCA G CCATCAACT    120

TCTAGTAGCA TTATTTATAG CAGCCAAGAA GATGTGAAAA AGTTTGAAAG G GAAGAAACC    180

CAAGACAAAG AAGAGAGTGT GGAATCTAGT TTGCCCCTTA ATGCCATTGA A CCTTGTGTG    240

ATTTGTCAAG GTCGACCTAA AAATGGTTGC ATTGTCCATG GCAAAACAGG A CATCTTATG    300

GCCTGCTTTA CATGTGCAAA GAAGCTAAAG AAAAGGAATA AGCCCTGCCC A GTATGTAGA    360

CAACCAATTC AAATGATTGT GCTAACTTAT TTCCCCTAG                             399

(2) INFORMATION FOR SEQ ID NO: 9:

(i) SEQUENCE CHARACTERISTICS:
        (A) LENGTH: 309 base pairs
        (B) TYPE: nucleic acid
        (C) STRANDEDNESS: single
        (D) TOPOLOGY: linear (xi) SEQUENCE DESCRIPTION: SEQ ID NO: 9:

ATGTGCAATA CCAACATGTC TGTACCTACT GATGGTGCTG TAACCACCTC A CAGATTCCA      60

GCTTCGGAAC AAGAGACCCT GGTTAGACCA AAGCCATTGC TTTTGAAGTT A TTAAAGTCT    120

GTTGGTGCAC AAAAAGACAC TTATACTATG AAAGAGGTTC TTTTTTATCT T GGCCAGTAT    180

ATTATGACTA AACGATTATA TGATGAGAAG CAACAACATA TTGTAAATGA T TGTGCTAAC    240

TTATTTCCCC TAGTTGACCT GTCTATAAGA GAATTATATA TTTCTAACTA T ATAACCCTA    300
```

-continued

```
GGAATTTAG                                                              309
```

(2) INFORMATION FOR SEQ ID NO: 10:

(i) SEQUENCE CHARACTERISTICS:
        (A) LENGTH: 1897 base pairs
        (B) TYPE: nucleic acid
        (C) STRANDEDNESS: single
        (D) TOPOLOGY: linear (xi) SEQUENCE DESCRIPTION: SEQ ID NO: 10:

```
CACAGATAAG GTTATTTGGG TACCCTCTCG AAAAGTTAAA CCGGACATCG C CCAAAAGGA      60
TGAGGTGACT AAGAAAGATG AGGCGAGCCC TCTTTTTGCA GGCTGGAGGC A CATAGATAA     120
GAGAATTATC ACTCTACATT CATCTTTCTC AAAGATTAAT CTACTTGTGT G TTTTATATT    180
TCATTAGAAT CGGACAGATG TTCAGTGCCA GCACCGGTGG CAGAAAGTAT T AAACCCAGA    240
ACTTAACAAA GGTCCATGGA CTAAAGAGGA GGATCAAAGG GTAATAGAAC A CGTGCAGAA    300
ATACGGTCCA AAGCGCTGGT CGGACATTGC TAAGCATTTG AAGGGAAGGA T TGGAAAACA    360
GTGCAGGGAG AGGTGGCACA ACCATCTGAA TCCAGAAGTG AAGAAAACCT C CTGGACAGA    420
AGAGGAAGAT AGAATTATTT ACCAGGCACA AAGAGACTG GGAAACAGAT G GGCAGAAAT    480
TGCAAAGTTG CTGCCTGGAC GGACTGATAA CGCTGTCAAG AACCACTGGA A TTCCACCAT    540
GCGCCGGAAG GTCGAGCAGG AGGGTTACCC GCAGGAGTCC TCCAAAGCCG G CCCGCCCTC    600
GGCAACCACC GGCTTCCAGA AGAGCAGCCA TCTGATGGCC TTTGCCCACA A CCCACCTGT    660
AGGCCCGCTC CCGGGGGCCG GCCAGGCCCC TCTGGGCAGT GACTACCCCT A CTACCACAT    720
TGCTGAGCCA CAAAATGTCC CTGGTCAGAT CCCATATCCA GTAGCACTGC A TATAAATAT    780
TATCAATGTT CCTCAGCCAG CTGCTGCAGC TATTCAGAGA CACTATACTG A TGAAGACCC    840
TGAGAAAGAA AAACGAATAA AGGAATTAGA GTTGCTACTT ATGTCGACTG A GAATGAACT    900
GAAAGGGCAG CAGGCATTAC AACACAGAA CCACACAGCA AACTACCCCG G CTGGCACAG    960
CACCACGGTT GCTGACAATA CCAGGACCAG TGGTGACAAT GCGCCTGTTT C CTGTTTGGG   1020
GGAACATCAC CACTGTACTC CATCTCCACC AGTGGATCAT GGTTGCTTAC C TGAGGAAAG   1080
TGCGTCCCCC GCACGGTGCA TGATTGTTCA CCAGAGCAAC ATCCTGGATA A TGTTAAGAA   1140
TCTCTTAGAA TTTGCAGAAA CACTCCAGTT AATAGACTCC TTCTTAAACA C ATCGTCCAA   1200
TCACGAGAAT CTGAACCTGG ACAACCCTGC ACTAACCTCC ACGCCAGTGT G TGGCCACAA   1260
GATGTCTGTT ACCACCCCAT TCCACAAGGA CCAGACTTTC ACTGAATACA G GAAGATGCA   1320
CGGCGGAGCA GTCTAGAGCT CAATTATAAT AATCTTGCGA ATCGGGCTGT A CGGGGCAA   1380
GGCTTGACCG AGGGGACTAT AACATGTATA GGCGAAAAGC GGGGTCTCGG T TGTAACGCG   1440
CTTAGGAAGT CCCCTCGAGG TATGGCAGAT ATGCTTTTGC ATAGGGAGGG G GAAATGTAG   1500
TCTTAATCGT AGGTTAACAT GTATATTACC AAATAAGGGA ATCGCCTGAT G CACCAAATA   1560
AGGTATTATA TGATCCCATT GGTGGTGAAG GAGCGACCTG AGGGCATATG G GCGTTAACA   1620
GAACTGTCTG TCCTTGCGTC ATTCCTCATC GGATCATGTA CGCGGCAGAG T ATGATTGGA   1680
TAACAGGATG GCACCATTCA TCGTGGCGCA TGCTGATTGG TGCGACTAAG G AGTTGTGTA   1740
ACCCACGAAT GTACTTAAGC TTGTAGTTGC TAACAATAAA GTGCCATTCT A CCTCTCACC   1800
ACATTGGTGT GCACCTGGGT TGATGGCCGG ACCGTCGATT CCCTGACGAC T GCGAACACC   1860
TGAATGAAGC TGAAGGCTTC AGGTACCCTT ACTTGAT                             1897
```

(2) INFORMATION FOR SEQ ID NO: 11:

(i) SEQUENCE CHARACTERISTICS:
        (A) LENGTH: 8082 base pairs
        (B) TYPE: nucleic acid
        (C) STRANDEDNESS: single
        (D) TOPOLOGY: linear (xi) SEQUENCE DESCRIPTION: SEQ ID NO: 11:

```
AGCTTGTTTG GCCGTTTTAG GGTTTGTTGG AATTTTTTTT TCGTCTATGT A CTTGTGAAT      60
TATTTCACGT TTGCCATTAC CGGTTCTCCA TAGGGTGATG TTCATTAGCA G TGGTGATAG     120
GTTAATTTTC ACCATCTCTT ATGCGGTTGA ATAGTCACCT CTGAACCACT T TTTCCTCCA     180
GTAACTCCTC TTTCTTCGGA CCTTCTGCAG CCAACCTGAA AGAATAACAA G GAGGTGGCT     240
GGAAACTTGT TTTAAGGAAC CGCCTGTCCT TCCCCCGCTG GAAACCTTGC A CCTCGGACG     300
CTCCTGCTCC TGCCCCCACC TGACCCCCGC CCTCGTTGAC ATCCAGGCGC G ATGATCTCT     360
GCTGCCAGTA GAGGGCACAC TTACTTTACT TTCGCAAACC TGAACGCGGG T GCTGCCCAG     420
AGAGGGGCG  GAGGGAAAGA CGCTTTGCAG CAAAATCCAG CATAGCGATT G GTTGCTCCC     480
CGCGTTTGCG GCAAAGGCCT GGAGGCAGGA GTAATTTGCA ATCCTTAAAG C TGAATTGTG     540
CAGTGCATCG GATTTGGAAG CTACTATATT CACTTAACAC TTGAACGCTG A GCTGCAAAC     600
TCAACGGGTA ATAACCCATC TTGAACAGCG TACATGCTAT ACACACACCC C TTTCCCCCG     660
AATTGTTTTC TCTTTTGGAG GTGGTGGAGG GAGAGAAAAG TTTACTTAAA A TGCCTTTGG     720
GTGAGGGACC AAGGATGAGA AGAATGTTTT TTGTTTTTCA TGCCGTGGAA T AACACAAAA     780
TAAAAAATCC CGAGGGAATA TACATTATAT ATTAAATATA GATCATTTCA G GGAGCAAAC     840
AAATCATGTG TGGGGCTGGG CAACTAGCTG AGTCGAAGCG TAAATAAAAT G TGAATACAC     900
GTTTGCGGGT TACATACAGT GCACTTTCAC TAGTATTCAG AAAAAATTGT G AGTCAGTGA     960
ACTAGGAAAT TAATGCCTGG AAGGCAGCCA AATTTTAATT AGCTCAAGAC T CCCCCCCCC    1020
CCCCAAAAAA AGGCACGGAA GTAATACTCC TCTCCTCTTC TTTGATCAGA A TCGATGCAT    1080
TTTTTGTGCA TGACCGCATT TCCAATAATA AAAGGGGAAA GAGGACCTGG A AAGGAATTA    1140
AACGTCCGGT TTGTCCGGGG AGGAAAGAGT TAACGGTTTT TTTCACAAGG G TCTCTGCTG    1200
ACTCCCCCGG CTCGGTCCAC AAGCTCTCCA CTTGCCCCTT TTAGGAAGTC C GGTCCCGCG    1260
GTTCGGGTAC CCCCTGCCCC TCCCATATTC TCCCGTCTAG CACCTTTGAT T TCTCCCAAA    1320
CCCGGCAGCC CGAGACTGTT GCAAACCGGC GCCACAGGGC GCAAAGGGGA T TTGTCTCTT    1380
CTGAAACCTG GCTGAGAAAT TGGGAACTCC GTGTGGGAGG CGTGGGGGTG G GACGGTGGG    1440
GTACAGACTG GCAGAGAGCA GGCAACCTCC CTCTCGCCCT AGCCCAGCTC T GGAACAGGC    1500
AGACACATCT CAGGGCTAAA CAGACGCCTC CCGCACGGGG CCCCACGGAA G CCTGAGCAG    1560
GCGGGGCAGG AGGGGCGGTA TCTGCTGCTT TGGCAGCAAA TTGGGGGACT C AGTCTGGGT    1620
GGAAGGTATC CAATCCAGAT AGCTGTGCAT ACATAATGCA TAATACATGA C TCCCCCCAA    1680
CAAATGCAAT GGGAGTTTAT TCATAACGCG CTCTCCAAGT ATACGTGGCA A TGCGTTGCT    1740
GGGTTATTTT AATCATTCTA GGCATCGTTT TCCTCCTTAT GCCTCTATCA T TCCTCCCTA    1800
TCTACACTAA CATCCCACGC TCTGAACGCG CGCCCATTAA TACCCTTCTT T CCTCCACTC    1860
TCCCTGGGAC TCTTGATCAA AGCGCGGCCC TTTCCCCAGC CTTAGCGAGG C GCCCTGCAG    1920
CCTGGTACGC GCGTGGCGTG GCGGTGGGCG CGCAGTGCGT TCTCTGTGTG G AGGGCAGCT    1980
GTTCCGCCTG CGATGATTTA TACTCACAGG ACAAGGATGC GGTTTGTCAA A CAGTACTGC    2040
TACGGAGGAG CAGCAGAGAA AGGGAGAGGG TTTGAGAGGG AGCAAAAGAA A ATGGTAGGC    2100
```

```
GCGCGTAGTT AATTCATGCG GCTCTCTTAC TCTGTTTACA TCCTAGAGCT A GAGTGCTCG      2160

GCTGCCCGGC TGAGTCTCCT CCCCACCTTC CCCACCCTCC CCACCCTCCC C ATAAGCGCC      2220

CCTCCCGGGT TCCCAAAGCA GAGGGCGTGG GGGAAAAGAA AAAAGATCCT C TCTCGCTAA      2280

TCTCCGCCCA CCGGCCCTTT ATAATGCGAG GGTCTGGACG GCTGAGGACC C CCGAGCTGT      2340

GCTGCTCGCG GCCGCCACCG CCGGGCCCCG GCCGTCCCTG GCTCCCCTCC T GCCTCGAGA      2400

AGGGCAGGGC TTCTCAGAGG CTTGGCGGGA AAAAGAACGG AGGGAGGGAT C GCGCTGAGT      2460

ATAAAAGCCG GTTTTCGGGG CTTTATCTAA CTCGCTGTAG TAATTCCAGC G AGAGGCAGA      2520

GGGAGCGAGC GGGCGGCCGG CTAGGGTGGA AGAGCCGGGC GAGCAGAGCT G CGCTGCGGG      2580

CGTCCTGGGA AGGGAGATCC GGAGCGAATA GGGGGCTTCG CCTCTGGCCC A GCCCTCCCG      2640

CTGATCCCCC AGCCAGCGGT CCGCAACCCT TGCCGCATCC ACGAAACTTT G CCCATAGCA      2700

GCGGGCGGGC ACTTTGCACT GGAACTTACA ACACCCGAGC AAGGACGCGA C TCTCCCGAC      2760

GCGGGGAGGC TATTCTGCCC ATTTGGGGAC ACTTCCCCGC CGCTGCCAGG A CCCGCTTCT      2820

CTGAAAGGCT CTCCTTGCAG CTGCTTAGAC GCTGGATTTT TTTCGGGTAG T GGAAAACCA      2880

GGTAAGCACC GAAGTCCACT TGCCTTTTAA TTTATTTTTT TATCACTTTA A TGCTGAGAT      2940

GAGTCGAATG CCTAAATAGG GTGTCTTTTC TCCCATTCCT GCGCTATTGA C ACTTTTCTC      3000

AGAGTAGTTA TGGTAACTGG GGCTGGGGTG GGGGTAATC CAGAACTGGA T CGGGGTAAA      3060

GTGACTTGTC AAGATGGGAG AGGAGAAGGC AGAGGGAAAA CGGAATGGT T TTTAAGACT      3120

ACCCTTTCGA GATTTCTGCC TTATGAATAT ATTCACGCTG ACTCCGGCC G GTCGGACAT      3180

TCCTGCTTTA TTGTGTTAAT TGCTCTCTGG GTTTTGGGGG CTGGGGGTT G CTTTGCGGT      3240

GGGCAGAAAG CCCCTTGCAT CCTGAGCTCC TTGGAGTAGG GACCGCATAT C GCCTGTGTG      3300

AGCCAGATCG CTCCGCAGCC GCTGACTTGT CCCCGTCTCC GGGAGGGCAT T TAAATTTCG      3360

GCTCACCGCA TTTCTGACAG CCGGAGACGG ACACTGCGGC GCGTCCCGCC C GCCTGTCCC      3420

CGCGGCGATT CCAACCCGCC CTGATCCTTT TAAGAAGTTG GCATTTGGCT T TTTAAAAAG      3480

CAATAATACA ATTTAAAACC TGGGTCTCTA GAGGTGTTAG GACGTGGTGT T GGGTAGGCG      3540

CAGGCAGGGG AAAAGGGAGG CGAGGATGTG TCCGATTCTC CTGGAATCGT T GACTTGGAA      3600

AAACCAGGGC GAATCTCCGC ACCCAGCCCT GACTCCCCTG CCGCGGCCGC C CTCGGGTGT      3660

CCTCGCGCCC GAGATGCGGA GGAACTGCGA GGAGCGGGGC TCTGGGCGGT T CCAGAACAG      3720

CTGCTACCCT TGGTGGGGTG GCTCCGGGGG AGGTATCGCA GCGGGTCTC T GGCGCAGTT      3780

GCATCTCCGT ATTGAGTGCG AAGGGAGGTG CCCCTATTAT TATTTGACAC C CCCCTTGTA      3840

TTTATGGAGG GGTGTTAAAG CCCGCGGCTG AGCTCGCCAC TCCAGCCGGC G AGAGAAAGA      3900

AGAAAAGCTG GCAAAAGGAG TGTTGGACGG GGGCGGTACT GGGGGTGGGG A CGGGGCGG      3960

TGGAGAGGGA AGGTTGGGAG GGGCTGCGGT GCCGGCGGGG GTAGGAGAGC G GCTAGGGCG      4020

CGAGTGGGAA CAGCCGCAGC GGAGGGGCCC CGGCGCGGAG CGGGGTTCAC G CAGCCGCTA      4080

GCGCCCAGGC GCCTCTCGCC TTCTCCTTCA GGTGGCGCAA AACTTTGTGC C TTGGATTTT      4140

GGCAAATTGT TTTCCTCACC GCCACCTCCC GCGGCTTCTT AAGGGCGCCA G GCCGATTT      4200

CGATTCCTCT GCCGCTGCGG GGCCGACTCC CGGGCTTTGC GCTCCGGGCT C CGGGGGAG      4260

CGGGGGCTCG GCGGGCACCA AGCCGCTGGT TCACTAAGTG CGTCTCCGAG A TAGCAGGGG      4320

ACTGTCCAAA GGGGGTGAAA GGGTGCTCCC TTTATTCCCC CACCAAGACC A CCCAGCCGC      4380

TTTAGGGGAT AGCTCTGCAA GGGGAGAGGT TCGGGACTGT GGCGCGCACT G CGCGCTGCG      4440
```

```
CCAGGTTTCC GCACCAAGAC CCCTTTAACT CAAGACTGCC TCCCGCTTTG T GTGCCCCGC      4500

TCCAGCAGCC TCCCGCGACG ATGCCCCTCA ACGTTAGCTT CACCAACAGG A ACTATGACC      4560

TCGACTACGA CTCGGTGCAG CCGTATTTCT ACTGCGACGA GGAGGAGAAC T TCTACCAGC      4620

AGCAGCAGCA GAGCGAGCTG CAGCCCCCGG CGCCCAGCGA GGATATCTGG A AGAAATTCG      4680

AGCTGCTGCC CACCCCGCCC CTGTCCCCTA GCCGCCGCTC CGGGCTCTGC T CGCCCTCCT      4740

ACGTTGCGGT CACACCCTTC TCCCTTCGGG GAGACAACGA CGGCGGTGGC G GGAGCTTCT      4800

CCACGGCCGA CCAGCTGGAG ATGGTGACCG AGCTGCTGGG AGGAGACATG G TGAACCAGA      4860

GTTTCATCTG CGACCCGGAC GACGAGACCT TCATCAAAAA CATCATCATC C AGGACTGTA      4920

TGTGGAGCGG CTTCTCGGCC GCCGCCAAGC TCGTCTCAGA GAAGCTGGCC T CCTACCAGG      4980

CTGCGCGCAA AGACAGCGGC AGCCCGAACC CCGCCCGCGG CCACAGCGTC T GCTCCACCT      5040

CCAGCTTGTA CCTGCAGGAT CTGAGCGCCG CCGCCTCAGA GTGCATCGAC C CCTCGGTGG      5100

TCTTCCCCTA CCCTCTCAAC GACAGCAGCT CGCCCAAGTC CTGCGCCTCG C AAGACTCCA      5160

GCGCCTTCTC TCCGTCCTCG GATTCTCTGC TCTCCTCGAC GGAGTCCTCC C CGCAGGGCA      5220

GCCCCGAGCC CCTGGTGCTC CATGAGGAGA CACCGCCCAC CACCAGCAGC G ACTCTGGTA      5280

AGCGAAGCCC GCCCAGGCCT GTCAAAAGTG GGCGGCTGGA TACCTTTCCC A TTTTCATTG      5340

GCAGCTTATT TAACGGGCCA CTCTTATTAG GAAGGAGAGA TAGCAGATCT G GAGAGATTT      5400

GGGAGCTCAT CACCTCTGAA ACCTTGGGCT TTAGCGTTTC CTCCCATCCC T TCCCCTTAG      5460

ACTGCCCATG TTTGCAGCCC CCCTCCCCGT TTGTCTCCCA CCCCTCAGGA A TTTCATTTA      5520

GGTTTTTAAA CCTTCTGGCT TATCTTACAA CTCAATCCAC TTCTTCTTAC C TCCCGTTAA      5580

CATTTTAATT GCCCTGGGGC GGGGTGGCAG GGAGTGTATG AATGAGGATA A GAGAGGATT      5640

GATCTCTGAG AGTGAATGAA TTGCTTCCCT CTTAACTTCC GAGAAGTGGT G GGATTTAAT      5700

GAACTATCTA CAAAAATGAG GGGCTGTGTT TAGAGGCTAG GCAGGGCCTG C CTGAGTGCG      5760

GGAGCCAGTG AACTGCCTCA AGAGTGGGTG GGCTGAGGAG CTGGGATCTT C TCAGCCTAT      5820

TTTGAACACT GAAAAGCAAA TCCTTGCCAA AGTTGGACTT TTTTTTTTCT T TTATTCCTT      5880

CCCCCGCCCT CTTGGACTTT TGGCAAAACT GCAATTTTTT TTTTTTTATT T TTCATTTCC      5940

AGTAAAATAG GGAGTTGCTA AAGTCATACC AAGCAATTTG CAGCTATCAT T TGCAACACC      6000

TGAAGTGTTC TTGGTAAAGT CCCTCAAAAA TAGGAGGTGC TTGGGAATGT G CTTTGCTTT      6060

GGGTGTGTCC AAAGCCTCAT TAAGTCTTAG GTAAGAATTG GCATCAATGT C CTATCCTGG      6120

GAAGTTGCAC TTTTCTTGTC CATGCCATAA CCCAGCTGTC TTTCCCTTTA T GAGACTCTT      6180

ACCTTCATGG TGAGAGGAGT AAGGGTGGCT GGCTAGATTG GTTCTTTTTT T TTTTTTTC      6240

CTTTTTTAAG ACGGAGTCTC ACTCTGTCAC TAGGCTGGAG TGCAGTGGCG C AATCAACCT      6300

CCAACCCCCT GGTTCAAGAG ATTCTCCTGC CTCAGCCTCC CAAGTAGCTG G GACTACAGG      6360

TGCACACCAC CATGCCAGGC TAATTTTTGT AATTTTAGTA GAGATGGGGT T TCATCGTGT      6420

TGGCCAGGAT GGTCTCTCCT GACCTCACGA TCCGCCCACC TCGGCCTCCC A AAGTGCTGG      6480

GATTACAGGT GTGAGCCAGG GCACCAGGCT TAGATGTGGC TCTTTGGGGA G ATAATTTTG      6540

TCCAGAGACC TTTCTAACGT ATTCATGCCT TGTATTTGTA CAGCATTAAT C TGGTAATTG      6600

ATTATTTTAA TGTAACCTTG CTAAAGGAGT GATTTCTATT TCCTTTCTTA A AGAGGAGGA      6660

ACAAGAAGAT GAGGAAGAAA TCGATGTTGT TTCTGTGGAA AAGAGGCAGG C TCCTGGCAA      6720

AAGGTCAGAG TCTGGATCAC CTTCTGCTGG AGGCCACAGC AAACCTCCTC A CAGCCCACT      6780

GGTCCTCAAG AGGTGCCACG TCTCCACACA TCAGCACAAC TACGCAGCGC C TCCCTCCAC      6840
```

```
TCGGAAGGAC TATCCTGCTG CCAAGAGGGT CAAGTTGGAC AGTGTCAGAG T CCTGAGACA      6900

GATCAGCAAC AACCGAAAAT GCACCAGCCC CAGGTCCTCG GACACCGAGG A GAATGTCAA      6960

GAGGCGAACA CACAACGTCT TGGAGCGCCA GAGGAGGAAC GAGCTAAAAC G GAGCTTTTT      7020

TGCCCTGCGT GACCAGATCC CGGAGTTGGA AAACAATGAA AAGGCCCCCA A GGTAGTTAT      7080

CCTTAAAAAA GCCACAGCAT ACATCCTGTC CGTCCAAGCA GAGGAGCAAA A GCTCATTTC      7140

TGAAGAGGAC TTGTTGCGGA AACGACGAGA ACAGTTGAAA CACAAACTTG A ACAGCTACG      7200

GAACTCTTGT GCGTAAGGAA AAGTAAGGAA AACGATTCCT TCTAACAGAA A TGTCCTGAG      7260

CAATCACCTA TGAACTTGTT TCAAATGCAT GATCAAATGC AACCTCACAA C CTTGGCTGA      7320

GTCTTGAGAC TGAAAGATTT AGCCATAATG TAAACTGCCT CAAATTGGAC T TTGGGCATA      7380

AAAGAACTTT TTTATGCTTA CCATCTTTTT TTTTTCTTTA ACAGATTTGT A TTTAAGAAT      7440

TGTTTTTAAA AAATTTTAAG ATTTACACAA TGTTTCTCTG TAAATATTGC C ATTAAATGT      7500

AAATAACTTT AATAAAACGT TTATAGCAGT TACACAGAAT TTCAATCCTA G TATATAGTA      7560

CCTAGTATTA TAGGTACTAT AAACCCTAAT TTTTTTTATT TAAGTACATT T TGCTTTTTA      7620

AAGTTGATTT TTTTCTATTG TTTTTAGAAA AAATAAAATA ACTGGCAAAT A TATCATTGA      7680

GCCAAATCTT AAGTTGTGAA TGTTTTGTTT CGTTTCTTCC CCCTCCCAAC C ACCACCATC      7740

CCTGTTTGTT TTCATCAATT GCCCCTTCAG AGGGCGGTCT TAAGAAAGGC A AGAGTTTTC      7800

CTCTGTTGAA ATGGGTCTGG GGGCCTTAAG GTCTTTAAGT TCTTGGAGGT T CTAAGATGC      7860

TTCCTGGAGA CTATGATAAC AGCCAGAGTT GACAGTTAGA AGGAATGGCA G AAGGCAGGT      7920

GAGAAGGTGA GAGGTAGGCA AAGGAGATAC AAGAGGTCAA AGGTAGCAGT T AAGTACACA      7980

AAGAGGCATA AGGACTGGGG AGTTGGGAGG AAGGTGAGGA AGAAACTCCT G TTACTTTAG      8040

TTAACCAGTG CCAGTCCCCT GCTCACTCCA AACCCAGGAA TT                         8082

(2) INFORMATION FOR SEQ ID NO: 12:

(i) SEQUENCE CHARACTERISTICS:
        (A) LENGTH: 4480 base pairs
        (B) TYPE: nucleic acid
        (C) STRANDEDNESS: single
        (D) TOPOLOGY: linear (xi) SEQUENCE DESCRIPTION: SEQ ID NO: 12:

AGGGTTACAC GTCTTAACTC AGAGTTGCAA CAGGCTTGAA CAAGCCCAGG C ACGCCCAGA       60

TACCTAGGGC CGAGTCACCG TTAAAACTAA CAGACCATAA AAGGAAAGGA A TACAGAACA      120

GACTAGGAGT ACCGGATCTG ACTCACAGGC CACCTGGCAG GAAGAGATAA G CCCCAGCCC      180

CCGACATTCA GGACGTCCCA GCCCGCACGT ACTCTTACCA TGTTACAACC T CATTCGAAT      240

ATGATTCAAA CCTGCCAATG TGTGTAGCTA TACCTTATCA CCTCATCTTG T GAAATAACC      300

AATCATATGT GAACATGTCT ATATGCTTCG TTTAAATCCA CCAATCCCCG T AACTATGCA      360

TCTGCTTCTG TACGCCCGCT TCTGCTTCCC CAAACCCTAT AAAAGCCCCA T GCTAGAGCT      420

GTTGGGCGCG CAAGTCCTCC GAAGAGACTG TGTGCCCGCA GGTACCTGTG T TTTCCAATA      480

AACCCTCTTG CTGATTGCAT CCGAGTGGCC TCGGCTCGGT CATTGGGCGC T TGGGGTCT      540

CCTCCTGAGG GAAAGGTCCT CTCCGGAGGT CTTTTCATTT TGGGGCTCG T CCGGGATCT      600

GGAGATCCTC CGCCCAGAGA TCACCGACCA CCCACCGGGA GGTAAGCCGG C CGGCATCTG      660

TCGTGTCTTG CCCTGTCTTG TCTTGTCTTG TCCTGTGCGC GTGTTCAGTT C GTCTCAGTT      720

TTGGACTCAG ATCTGGGTTT TGGTCGAAGG AGAAGGCCCA GGGCTTCGGT T TCTCAGGGT      780
```

| | |
|---|---|
| TCAGGACCCT CAGCGCCTCC GTTTGGGCGG GTCAGAGAAG GAGCTGACGA G CTCGGACTT | 840 |
| CTCCCCCCGC AGCCCTGGAA GACGTTCCAA GGGTGTCTGG AGCCCGGTTC T TTGGGGCTC | 900 |
| AGCCCGTATC GGAGGGATAC GTGGTTTTGG TTGGAGGAGA GGGTCCAGGA C CCTCGGCAC | 960 |
| CTCCATCTGA CTCTTTGTTT TGGGTTTTAC GTCGAAGCCG CGCGGCGCGT C TGTCTGTTA | 1020 |
| TTTGTCTGAT CGTTGGATTT GTCTGTCTAA TCTGTGCCCT AATTTTCTTT G AAGCTACCA | 1080 |
| TGGGACAATC GCTAACAACC CCCTTGAGTC TCACTCTAGA CCATTGGAAG G ACGTCCGAG | 1140 |
| ACCGAGCACG TGATCAGTCG GTCGAGATCA AGAAAGGTCC TCTCCGGAGG T CGGGGACAG | 1200 |
| TCGCGCCAGC AAGCGGTGGG GCAGGAGCTC CTGGTTTGGC AGCCCCTGTA G AAGCGATGA | 1260 |
| CAGAATACAA GCTTGTGGTG GTGGGCGCTA GAGGCGTGGG AAAGAGTGCC C TGACCATCC | 1320 |
| AGCTGATCCA GAACCATTTT GTGGACGAGT ATGATCCCAC TATAGAGGAC T CCTACCGGA | 1380 |
| AACAGGTAGT CATTGATGGG GAGACGTGTT TACTGGACAT CTTAGACACA G CAGGTCAAG | 1440 |
| AAGAGTATAG TGCCATGCGG GACCAGTACA TGCGCACAGG GGAGGGCTTC C TCTGTGTAT | 1500 |
| TTGCCATCAA CAACACCAAG TCCTTTGAAG ACATCCATCA GTACAGGGAG C AGATCAAGC | 1560 |
| GGGTGAAAGA TTCAGATGAT GTGCCAATGG TGCTGGTGGG CAACAAGTGT G ACCTGGCCG | 1620 |
| CTCACACTGT TGAGTCTCGG CAGGCCCAGG ACCTTGCTCG CAGCTATGGC A TCCCCTACA | 1680 |
| TTGAAACATC AGCCAAGACC CGACCAGGTG TGGAGGATGC CTTCTACACA C TAGTACGTG | 1740 |
| AGATTCGGCA GCATAAACTG CGGAAACTGA ACCCGCCTGA TGAGTGGCC C CTGGCTGCA | 1800 |
| TGAGCTGCAA GTGTGTGCTG TCCTGACACC AGGTTAAGGA CCTGATTTTC C GCCAGAAGC | 1860 |
| CGTACGGACA CCCTGACCAG GTGGCCTACA TTGTCACCTG GGAGAGCTTG G CATTTAGCC | 1920 |
| CTCCTCCTTG GGCAGAACCC TTTGTGGACC CGAATTGGCT TCCTGTTTCC C CTAAACCTG | 1980 |
| TTTCCCCGAG CCCACCTGAC CCTTTGGTTG CTTCTTCCTC TCTCTATCCT G CTCTAACTA | 2040 |
| AGGAAGAATC TCCCAAAGTC CCTCCCCCGA AACCTGTCCT CCCAGAGGAC C CAAATTCCC | 2100 |
| CCCTTATAGA TCTCCTGTTG AAGAACCTC CTCCCGTACCC TGTACCTACA G CCCCGCCAA | 2160 |
| GAGAAGAGGA AGTGGAGCCG CCTGCTAGAC CTCGACTCGA GGCGGCCCCT T CCCCTGTGG | 2220 |
| CTGGAAGACT TCGGGACGA CGCGAGGTGG CGCCAGACTC CACCTCCCAG G CCTTTCCGC | 2280 |
| TTAGACAAGG GGCTGGCGGC CAGATACAAT ACTGGCCATT CTCAGCGGCC G ACATATATA | 2340 |
| ACTGGAAACA ACACAACCCC CCCTTTTCTA AGGATCCGGT GGCTCTCACC A ACCAGATAG | 2400 |
| AATCTGTCTT GCTTACCCAT CAGCCCACTT GGGATGATAT ACAGCAACTT T TACAGGCCC | 2460 |
| TCCTGACCTC TGAAGAGAAG CAGAGAGTGC TCTTAGAGGC CAGGAAACAT G TTTTGGGGG | 2520 |
| ACAATGGACG CCCCACCTTG CTCCCGAAAG AGATCGATGA TGCATTCCCA C TTACAAGAC | 2580 |
| CTGATTGGGA TTTCACCACG GCTAAAGGTA GGAGACACCT ACGCCTTTAT C GCCAGTTGC | 2640 |
| TCCTAGCGGG TCTCCGAGGG GCGGCACGAC GCCCCACCAA TTTGGCTCAG G TAAAACAAG | 2700 |
| TGGTACAAGA GGCTGCGGAG ACTCCCTCAG CCTTCCTAGA GAGACTTAAG G AAGCTTATC | 2760 |
| GCATGTATAC CCCTTATGAT CCAGATGATC CAGGACAAAT GACAAATGTC T CCATGTCCT | 2820 |
| TCATCTGGCA GGCAGCACCA GATATCAGGG CCAAGCTACA GAGAATAGAA A ATTTACAAG | 2880 |
| GGTATACACT GCAGGATTTA CTTAAGGAGG CAGAAAGAAT TTATAACAAG A GAGAGACAC | 2940 |
| AAGAAGAAAA GAAAGATAAA ATACGTAGAG AAAAAGATGA GAGAGACCGA A AAAGAAACA | 3000 |
| GAGAGTTGAG TCGAATCTTG GCCGCCGTAG TTCAGGGTCA AGAGAAAAGG G GAGAGAGGG | 3060 |
| TGGGAGTTCG AAAGGGGCCA AAGCTAGATA AGGATCAATG TGCGTATTGC A AAGAAAGAG | 3120 |

```
GACACTGGGC CAGAGATTGC CCTAAGAAAC CCAGCGGCTC CGAAGACCCC G CCCACAGAC    3180

CTCCCTCTTG GCCCTAGATA AAGATTAGGG AGGTCAGGGC CAGGAGCCCC C CCCTGAGCC    3240

CAGGATAACT CTTGAAGTTG GGGGGCAGCC AGTCACCTTT CTGGTGGACA C AGGAGCCCA    3300

GCACTCAGTC CTCACCCAGG CCCCTGGACA ACTCAGCGAC CGGACGGCCT G GGTACAAGG    3360

AGCCACTGGC AGCAAGAGAT ACCGTTGGAC TACAGATCGA CGGGTTCAGC T GGCTACTGG    3420

TAAGGTGACC CATTCCTTCT TACATGTTCC GGACTGCCCA TACCCTCTGC T GGGCCGTGA    3480

CTTGCTTACC AAATTAAAAG CTCAGATCCA TTTTGAAGAA GGAGGGACCC G AGTAACCGG    3540

GCCCCGCGGT ATTCCTCTTC AGATTTTAAC CCTTCAGTTA GAAGATGAAT A TAGATTATA    3600

TGAACCAGAA CAGGACAAGC CAAAATCTCC AGAAATAGAC TCTTGGGTCA C GAAATTCCC    3660

ACTGGCCTGG GCAGAGACTG GCGGGATGGG GTTGGCGCTC CAACAGCCTC C CCTAATTAT    3720

CCAGTTAAAG GCCACCGCGA CTCCTGTCTC CATTAAACAG TACCCCATGT C ATGGGAAGC    3780

TTATCAGGGC ATAAAGCCAC ATATCAGGAG GCTCTTAGAC CAAGGCATCC T AGTCCCTTG    3840

CCGGTCACCC TGGAATACGC CTCTGCTACC TGTTAAGAAG CCCGGCACTG G AGACTATAG    3900

GCCAGTACAA GATTTGAGAG AGGTCAACAA AAGAGTAGAA GATATTCATC C AACTGTCCC    3960

AAACCCTTAT AACCTACTCA GCACCCTGCC TCCCACCCAT ACTTGGTATA C GGTCTTAGA    4020

TCTGAAGGAT GCTTTCTTCT GCCTCCGGCT GAGCCCAGAA AGCCAGCCCT T ATTTGCTTT    4080

TGAGTGGAAA GACTCTGAAA TGGGGCTTTC GGGACAGTTG ACTTGGACAA G GTTACCACA    4140

GGGTTTCAAA AACAGCCCAA CGCTCTTTGA TGAGGCCTTA CACCGGGACT T GGCTGACTT    4200

TCGAGTCCAG CATCCCACTC TTATACTTCT TCAGTTTGTT GATGACCTTC T TCTAGGGGC    4260

CACTTCTGAG ACAGCATGCC ACCAGGGAAC AGAATCCCTC TTGCAGACTT T GGGGCGATT    4320

GGGCTATCGA GCTTCTGCCA GAAAGGCTCA AATTTGCCAG ACCCAGGTTA C TTATTTAGG    4380

CTATCAACTA AGGGATGGAC AGCGATGGCT GACTCCGGCT AGGAAACAGA C CGTGGCCAA    4440

CATCCCAGCC CCAAGAAATG GCCGACAGCT ACGGGAATTC                          4480

(2) INFORMATION FOR SEQ ID NO: 13:

(i) SEQUENCE CHARACTERISTICS:
        (A) LENGTH: 565 base pairs
        (B) TYPE: nucleic acid
        (C) STRANDEDNESS: single
        (D) TOPOLOGY: linear (xi) SEQUENCE DESCRIPTION: SEQ ID NO: 13:

GCTGAGTAGT GCGCGAGCAA AATTTAAGCT ACAACAAGGC AAGGCTTGGC C GACAATTGC     60

ATGAAGAATC TGCTTAGGGT TAGGCGTTTT GCGCTGCTTC GCGATGTACG G GCCAGATAT    120

ACGCGTATCT GAGGGACTA GGGTGTGTTT AGGCGAAAAG CGGGGCTTCG G TTGTACGCG    180

GTTAGGAGTC CCCTCAGGAT ATAGTAGTTT CGCTTTTGCA TAGGGAAGGG G AAATGTAGT    240

CTTATGCAAT ACTCTTGTAG TCTTGCAACA TGCTTATGTA ACGATGAGTT A GCAACATGC    300

CTTACAAGGA GAGAAAAAGC ACCGTGCATG CCGATTGGTG GAAGTAAGGT G GTACGATCG    360

TGCCTTATTA GGAAGGCAAC AGACGGGTCT GACATGGATT GGACGAACCA C CGAATTCCG    420

CATTGCAGAG ATATTGTATT TAAGTGCCTA GCTCGATACA ATAAACGCCA T TTGACCATT    480

CACCACATTG GTGTGCACCT GGGTTGATGG CCGGACCGTT GATTCCCTGA C GACTACGAG    540

CACCTGCATG AAGCAGAAGG CTTCA                                          565

(2) INFORMATION FOR SEQ ID NO: 14:
```

(i) SEQUENCE CHARACTERISTICS:
    (A) LENGTH: 1804 base pairs
    (B) TYPE: nucleic acid
    (C) STRANDEDNESS: single
    (D) TOPOLOGY: linear (xi) SEQUENCE DESCRIPTION: SEQ ID NO: 14:

```
GGATCCTCAG GGGTAACACC TTTTGGAGGT GGGCATCTTC CTCATTCTCA G TGGTGCCAA      60

GTTCATATCC TGCTGGCTTA ACACGTGGTG TTACTATATT TGTGGCCTTA T ATGATTATG     120

AAGCTAGAAC TACAGAAGAC CTTTCATTTA AGAAGGGTGA AAAATTTCAA A TAATTAACA     180

ATACAGAAGG AGACTGGTGG GAAGCAAGAT CAATCACTAC AGGAAAGAAT G GTTATATCC     240

TGAGCAGTTA TGTAGCGCCT GCAGATTCCA TTCAGGCAGA AGAATGGTAT T TTGGCAAAA     300

TGGGGAGAAA AGATGCTGAA AGATTACTTC TGAATCCTGG AAATTAATGA G GTATTTTCT     360

TAGGAAGAGA GAGTGAAATG GCTGGGTGCA GTGGCTCATG CCTGTAATCC C AGCACTTTG     420

GGAGGCCGAG TTGGGCGGAT CACCTGAGGT CAGGAGTTCG AGACTAGCCT G GCCAACATG     480

GTGAAACCCC ATCTCTACTA AAAAAAAAAG TACAAAATTA GCTGGACGTG G TGGTGAGTG     540

CCTGTAATCC CAGCTACTCA GGAGGCTGAG GCAGCAGAAT CACTTGAACC T GGGAGGCGG     600

AGGTTGCAGT GAGCTGAGAT CGCGCCACTG CACTCCAGCC TCGGCGACAA G AGCAAAAAC     660

TCCGTCTAAA AAACAAATAA GCAAACAGAA CAAAACAAAA CAAAAACGAG A GAGCGAAAC     720

TACTAAAGGT GCTTATTCCC TCTCTATTCG TGATTGGGAT GAGGTAAGGG G TGACAATGT     780

GAAACACCAC AAAATTAGGA AACTTGACAA TGGTAGATAC TATATCACAA C CAGAGAACA     840

ACTTGATACT CTGCAGAAAT TGGCAAAACA CTACACAGAA CATGCTGATG G TTTATGCCA     900

CAAGTTAACA ACTGTGTGTC CAACTGTGAA ACCTCAGATT CAAGGTCTAG C AAAAGATGC     960

TTGGGAAATC CCTTGATAAT CTTTGCGACT AGAGGTTAAA CTAGGACAAG G ATGTTTTGG    1020

CAAAGTGTGG ATGGGAATAT GGAATGGAAC CACAAAAGTA GCAATCAAAA C ACTAAAACC    1080

AGGTACAATG ATGCCAGAAG CTTTTCTTCA AGAAGCTCAG GTAATGAAAA A AATAAGACA    1140

TGGTAAACTT GTTCCACTAT ATGCTGTTGT TTCTGAAGAG CCAATTTACA T TGTCACTGA    1200

ATTGATGTCA AAAGGAAGCT TATTCAATTT CCTTAAGGAA GGAGATGGAA A GTATTTGAA    1260

GCTTCCACAA ATGGTTGATA TGCCTGCTCA GATTGCTGAT GGTATGGCAT A TATTAAAAG    1320

AATGAACTAT ATTCACCGAG ATCTCTGGGC TGCTAATATT CTTGTAGGAG A AAATCTTCT    1380

GTGCAAAATA GCAGATTTTG GTTTAGCAAG GTTAATTGAA GACAATGAAT A CACATCAAG    1440

ACAAGGTGCA GAATTTCCAA TCAAATGGAC AGCTCCTGAA GTTGCACTGT A TGGTGGGTT    1500

TACAATAAAG TCTGGTGTCT GCTCATTTGG AATTCTACAG ACAGAACTGG T AACAAAGGG    1560

CAGAGTGCCA TATCCAGGTA TGGTGAACCA TGAAATACTG GAACAGGTGG A GCGAGGATA    1620

CAGGATGCCT TGCCCTCAGG GCTGTCCAGA ATCCCTCCAT GAATTGATGA A TCTGTGTTG    1680

GAAGAAGGAC CCTGATGAAA GACCAACATT TGAATATGTT CAGTCCTTCT T GGGAGACTA    1740

CTTCACTGCT ACAGAGCCAT AGTACCAGCC AGGAGAAAAC TTCTAATTCA A GTAGCCTAT    1800

TTTA                                                                 1804
```